(12) United States Patent
Bartelmez et al.

(10) Patent No.: US 6,841,542 B2
(45) Date of Patent: Jan. 11, 2005

(54) TRANSFORMING GROWTH FACTOR BETA (TGF-β) BLOCKING AGENT-TREATED STEM CELL COMPOSITION AND METHOD

(75) Inventors: Stephen H. Bartelmez, Seattle, WA (US); Patrick L. Iversen, Corvallis, OR (US)

(73) Assignee: AVI BioPharma, Inc., Corvallis, OR (US)

(*) Notice: Subject to any disclaimer, the term of this patent is extended or adjusted under 35 U.S.C. 154(b) by 0 days.

(21) Appl. No.: 09/900,115

(22) Filed: Jul. 6, 2001

(65) Prior Publication Data

US 2003/0109465 A1 Jun. 12, 2003

Related U.S. Application Data

(60) Provisional application No. 60/216,256, filed on Jul. 6, 2000.

(51) Int. Cl.[7] .................. C07H 21/04; A61K 48/00; C12N 15/00
(52) U.S. Cl. .................. 514/44; 435/325; 435/377; 435/375; 536/23.1; 536/24.1; 536/24.5
(58) Field of Search .................. 435/325, 377, 435/375; 514/44; 536/23.1, 24.1, 24.5

(56) References Cited

U.S. PATENT DOCUMENTS

| 5,801,154 A | 9/1998 | Baracchini et al. |
| 5,958,774 A | 9/1999 | Klein et al. |

OTHER PUBLICATIONS

Written Opinion mailed Oct. 30, 2002, from IPA/US, Commissioner of Patents and Trademarks, for Int'l. application No. PCT/US01/21420; Int'l. Filing Date: Jul. 6, 2001.

Batard, P., et al., "TGF–β1 maintains hematopoietic immaturity by a reversible negative control of cell cycle and induces CD34 antigen up–modulation," *Journal of Cell Science,113*:383–390 (2000).

Fortunel, N., et al., "Transforming growth factor–β: pleiotropic role in the regulation of hematopoiesis," *Blood, 95*:(6) 2022–2036 (2000).

Hatzfeld, J., et al., "Release of Early Human Hematopoietic Progenitors from Quiescence by Antisense Transforming Growth Factor β1 or Rb Oligonucleotides," *J. Exp. Med., 174*:925–929 (1991).

Hudziak, R.M., et al., "Antiproliferative Effects of Steric Blocking Phosphorodiamidate Morpholino Antisense Agents Directed against c–myc," *Antisense and Nucleic Acid Drug Development, 10*:163–176 (2000).

Hudziak, R.M., et al., "Resistance of Morpholino Phosphorodiamidate Oligomers to Enzymatic Degradation," *Antisense and Nucleic Acid Drug Development, 6*:267–272 (1996).

Summerton, J., et al., "Morpholino Antisense Oligomers: Design, Preparation, and Properties," *Antisense and Nucleic Acid Drug Development, 7*:187–195 (1997).

*Primary Examiner*—Sean McGarry
(74) *Attorney, Agent, or Firm*—Perkins Coie LLP

(57) ABSTRACT

The invention relates to TGF-β blocking agent-treated HSC compositions and methods comprising the same. The TGF-β blocking agent-treated stem cells are viable for an extended time in culture without replication or differentiation and upon transfer to appropriate conditions are capable of long term hematopoietic reconstitution.

6 Claims, 3 Drawing Sheets

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1
gagggcggca tggggaggc                                          20

<210> SEQ ID NO 2
<211> LENGTH: 21

```
<212> TYPE: DNA
<213> ORGANISM: Artificial Sequence
<220> FEATURE:
<223> OTHER INFORMATION: synthetic oligonucleotide

<400> SEQUENCE: 2
gacccatggc agcccccgtc g                                              21

<210> SEQ ID NO 3
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 3
gctgtgcgcg cgccttctct atg                                            23

<210> SEQ ID NO 4
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 4
gtgaacgaca tcycatctag g                                              21

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
gcagcagttc ttctccgtgg                                                20
```

TRANSFORMING GROWTH FACTOR BETA (TGF-β) BLOCKING AGENT-TREATED STEM CELL COMPOSITION AND METHOD

This application claims benefit of priority to U.S. Provisional Application Ser. No. 60/216,256, filed Jul. 6, 2000, expressly incorporated by reference herein.

FIELD OF THE INVENTION

The present invention relates to in vitro or ex vivo cultured stem cell compositions comprising stem cells treated with a TGF-β blocking agent and to methods for producing the same, wherein the compositions are characterized by an increase in the survival time of long term repopulating hematopoietic stem cells (LTR-HSC) without replication or differentiation. The invention also relates to methods that promote the rapid engraftment of LTR-HSC following in vivo administration and to methods that facilitate the rapid proliferation of LTR-HSC in vitro.

References

Akhtar, S., et al., *Nucleic Acids Res.* 19(20):5551–9, 1991.
Anderson, K. P., et al., *Antimicrob. Agents and Chemotherapy* 40(9):2004–2011, 1996.
Anderson, C. M., et al., *J Neurochem.* 73(2):867–73, 1999.
Andrews R G et al., *J Exp Med* 172(1):355–8, 1990.
Baker, et al, *Nucleic Acids Res.* 18(12):3537–43, 1990.
Bartelmez S, et al., "Functional resolution of hematopoietic long-term and short-term marrow repopulating stem cells in vitro," submitted to *Blood*, 2000.
Bennett et al., *Circulation* 92(7):1981–93, 1995.
Bertoncello I et al., *Exp Hematol* 19(2):95–100, 1991.
Beutler E, *Biol Blood Marrow Transplant* 5(5):273–6, 1999.
Bjornson C R R et al., *Science* 283:534–7, 1999.
Blaese R M, et al., *Science* 270, 475–480, 1995.
Cardoso A A et al., *PNAS USA*, 90:8707–8711, 1993.
Cashman et al., *Blood* 75:96–101, 1990.
Cohen et al., *Antisense Res. & Dev.* 2:191, 1991.
Cooney, et al., *Science* 241:456, 1988.
Dao M, *Leukemia* 13(10):1473–80, 1999.
Dervan, et al. *Science* 251:1360, 1991.
Dexter T M et al., *Prog Clin Biol Res* 148, 13–33, 1984
Dick J E et al *Cell* 42, 71–9, 1985.
Dzau V, Keystone Symposium Molecular and Cellular Biology of Gene Therapy, Keystone, Co. Jan. 19–25, 1998.
Ellingsworth L R et al, *J. Biol. Chem*, 261: 12362–12367, 1986.
Fortunel N et al., J Cell Sci. 111:1867–1875, 1998.
Hatzfeld J et al., *J Exp Med*, 174: 925–929, 1991.
Hatzfeld A et al., *Hum Gene Ther Jan* 20:7(2):207–13; 1996.
Hudziak, R. M et al., *Antisense Nucleic Acid Drug Dev*, 6:267–272, 1996.
Imbert A M et al., *Exp Hematol* 26(5):374–81, 1998.
Isner J, Keystone Symposium Molecular and Cellular Biology of Gene Therapy, Keystone, Co. Jan. 19–25, 1998.
Jakobovits, A, et al., *Ann N Y Acad Sci* 764:525–35, 1995.
Jakobovits, A, *Curr Opin Biotechnol* 6(5):561–6, (1995).
Jones, R. J., et al., *Nature* 347(6289):188–9, 1990.
Jordan C T et al., *Genes Dev* 4, 220–32, 1990.
Keller G and Snodgrass R *J Exp Med* 171, 1407–18, 1990.
Ku H et al., *Blood* 87, 4544–51, 1996.
Lee, et al., *Nucl. Acids Res.* 6:3073, 1979.
Li and Johnson, *Blood* 15;84(2):408–14, 1994.
Loke, S. L., et al., *Proc Natl Acad Sci U S A.* 86(10): 3474–8, 1989.
Lucas C et al., *J Immunol.*, 145:1415–1422, 1990.
McNiece, I. K., *Int J Cell Cloning* 8(3):146–60, 1990.
Ogawa M et al., *Stem Cells* 15 Suppl 1, 7–11, 1997.
Matsunaga T et al., *Blood* 92, 452–61, 1998.
Ohta M et al., *Nature*, 329:539–541, 1987.
Osawa M et al., *Science* 273, 242–245, 1996.
Ottmann et al., *J. Immunol.* 140:2661–2665, 1988.
Pari, G. S., et al., *Antimicrob. Agents and Chemotherapy* 39(5):1157–1161, 1995.
Peters S O et al., *Blood.* 87(1):30–7. 1996.
Petersen B E et al., *Science* 284:1168–70, 1999.
Pettengell R et al., *Blood* 84(11):3653–9, 1994.
Ploemacher R E et al. *Stem Cells* 11:336–347, 1993.
Ramsfjell V et al., *Blood* 88, 4481–92, 1996.
Sitnicka E et al, *Blood*, 88(1):82–88, 1996.
Sitnicka E et al., *Blood* 87:4998–5005, 1996.
Smith, L G et al., *Proc Natl Acad Sci U S A* 88, 2788–92, 1991.
Soma T et al., *Blood*, 87(11):4561–7, 1996.
Spitzer and Eckstein, *Nucleic Acids Res.* 16(24): 11691–704, 1988.
Summerton, J and Weller D, *Antisense Nucleic Acid Drug Dev.*, 7:187–195, 1997.
Tanaka, J, et al., *Int J Hematol* 69(2):70–4, 1999.
Taswell C., *J Immunol* 126, 1614–9, 1981.
Waegell W O et al., *Exp Hematol*, 22(11):1051–7, 1994.
Wingo P A, et al., *Cancer* 82(6), 1197–1207, 1998.
Wolf N S et al., *Exp Hematol* 21(5):614–22, 1993.
Wu W J and Wu T L, *J Microencapsul.* 16(5):639–46, 1999.
Yagi M et al., *Proc. Nat. Acad. Sci.* 96:8126–8131, 1999.
Yakubov, L. A., et al., *Proc Natl Acad Sci U S A.* 86(17):6454–8, 1989.
Yonemura Y et al., *Proc Natl Acad Sci U S A.* 93(9): 4040–4, 1996.
Yoshida M et al., *Br J Haematol* 98, 254–64, 1997.
Young J C et al., *Blood* 88, 1619–31, 1996. Yu J et al., *Gene Ther* 5(9):1265–71, 1998.
Zanjani E D et al., *Stem Cells* 13(2):101–11, 1995.

BACKGROUND OF THE INVENTION

The hematopoietic stem cell (HSC) is a pluripotent progenitor cell that has been characterized as a cell that is transplantable and can self-replicate or generate daughter cells that are destined to commit to mature cells of different specific lineages.

Self-replication of the most primitive HSC produces daughter cells that possess a long (possibly unlimited) clonal lifespan, while differentiation of HSCs results in a loss of such multilineage potential, and corresponding lineage commitment with a progressive reduction in their clonal lifespan. Previous studies indicate that the proliferation of HSC ex vivo appears to favor differentiation at the expense of self-replication, eventually resulting in a complete loss of HSC. Previous studies indicated that survival of HSC ex vivo in the absence of growth factors is limited, resulting in a complete loss of HSC after about 0.5–4 days in culture (Ploemacher et al., 1993; Li et al., 1994).

In contrast, transplantation studies have shown that a single HSC can repopulate the marrow of a lethally irradiated mouse, demonstrating that self-renewal of HSC occurs in vivo, as indicated by transplantation studies wherein a single HSC repopulated the marrow of an immunodeficient mouse (Smith, et al., 1991: Osawa et al., 1996). In addition, repopulation of secondary (and tertiary) recipients, has been demonstrated (Dick et al., 1985; Jordan et al., 1990; Keller et al., 1990). HSC have also been demonstrated to be capable of repopulating non-hematopoietic human tissues, including but not limited to liver (Petersen et al., 1999) and neuronal tissue (Bjornson et al., 1999).

Clinical trials are underway using treatment regimens that includes high-dose chemotherapy and/or radiation therapy together with bone marrow transplantation or transplantation of an HSC-containing cell population for the treatment of various cancers, including ovarian cancer, thymomas, germ cell tumors, multiple myeloma, melanoma, testicular cancer, lung cancer, and brain cancer.

Cell preparations enriched for hematopoietic stem cells generally contain a low percentage of cells capable of long-term hematopoietic reconstitution. In general, culture conditions effective to promote the survival of hematopoietic stem cells include cytokines, which stimulate cell division and differentiation of the cells, diminishing their long term repopulating capability. Frequently, as a result, in vivo administration of such cell preparations does not result in rapid repopulation of the host hematopoietic system. In particular, the slow repopulation of the neutrophil and platelet compartments of the hematopoietic system complicates the recovery process and may result in susceptibility to infection and/or complications due to poor blood clotting.

Transforming growth factor beta-1 (TGF-β1) is known to directly and reversibly inhibit the initial cell divisions of long-term repopulating hematopoietic stem cells (LTR-HSC) in vitro. (See, e.g., Sitnicka et al, 1996 and Ploemacher et al., 1993; Ottmann et al., 1988; Cashman et al., 1990.) The in vivo administration of TGF-β to humans to enhance the number of hematopoietic progenitor cells in peripheral blood has also been described. (See, e.g. U.S. Pat. No. 5,674,843, issued Oct. 7, 1997.) In addition, the release of CD34 positive human hematopoietic progenitor cells from quiescence has been reported following treatment with a phosphorothioate antisense oligomer to TGF-β1 or Rb1 in culture medium in the presence of cytokines and/or growth factors (Hatzfeld et al., 1991).

Although inhibition of genes associated with cellular development has been achieved using antisense technology, naturally occurring oligonucleotides have a nuclease-sensitive phosphodiester backbone. However, it has also been demonstrated that naturally occurring oligonucleotides can be modified rendering them resistant to degradation by nucleases, e.g., by incorporating a methylphosphonate, phosphorothioate or phosphodiamidate linkage into the oligonucleotide sequence in place of the standard phosphodiester linkage (Spitzer and Eckstein, 1988; Baker, et al, 1990; Hudziak, 1996).

For therapeutic purposes, it would be desirable to be able to regulate the differentiation of hematopoietic stem cells in vitro (ex vivo) and in vivo using an agent which acts specifically on hematopoietic stem cells and which is not sensitive to enzymatic degradation in cell culture or in vivo.

SUMMARY OF THE INVENTION

The present invention provides stem cell composition capable of rapid in vivo repopulation of the hematopoietic system of a subject and methods for making the same. The compositions of the invention comprises a cell population enriched for hematopoietic stem cells (HSC) and treated with a TGF-β blocking agent under culture conditions effective to block the effect of TGF-β on replication and/or differentiation of the stem cells.

Preferred targets for the TGF-β blocking agents of the invention include TGF-β and factors involved in the TGF-β receptor signaling pathway.

In one aspect, preferred TGF-β blocking agents are morpholino oligomers containing (i) from 8 to 40 nucleotides, (ii) a targeting nucleic acid sequence complementary to a nucleic acid sequence which encodes TGF-β or a factor involved in the TGF-β receptor signaling pathway, and (iii) uncharged, phosphorous-containing intersubunit linkages.

In one preferred embodiment, such morpholino oligomers have the phosphorodiamidate linkage represented at FIG. 2B-B, where $X=NH_2$, $Y=O$, and $Z=O$ and a length of from 12 to 25 bases.

Exemplary preferred antisense oligomers have a sequence presented as SEQ ID NO:1, SEQ ID NO:2 or SEQ ID NO:5.

In another aspect, a stem cell composition of the invention comprises human hematopoietic stem cells, characterized as lacking the expression of lineage markers (lin-), and either (a) positive for cell surface expression of CD 34 and KDR and negative for cell surface expression of CD38 or (b) positive for cell surface expression of both CD 34 and Thy1.

Conditions effective to block the effect of TGF-β on replication and/or differentiation of stem cells include culture medium lacking exogenously provided cytokines.

The invention also provides a method of prolonging the survival time of human stem cells in culture, by obtaining a population of cells containing HSC, enriching for stem cells population and exposing the cells, ex vivo, to a TGF-β blocking agent under culture conditions, and for a period of time, effective to preserve the viability and differentiation state of the stem cells. These cells may be maintained in vitro for an extended period of time, and may be used for in vivo transfer into a subject in need of hematopoietic reconstitution or the TGF-β blocking agent-treated stem cells may be cultured under conditions effective to result in rapid proliferation and differentiation of the cells into lineage committed progenitor cells and their progeny.

These and other objects and features of the invention will become more fully apparent when the following detailed description is read in conjunction with the accompanying figures and examples.

DETAILED DESCRIPTION OF THE INVENTION

I. Definitions

Figure 1A:
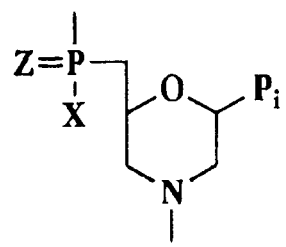
FIGS. 1A–D show several preferred morpholino-type subunits having 5-atom (A), six-atom (B) and seven-atom (C–D) linking groups suitable for forming polymers.

The terms below, as used herein, have the following meanings, unless indicated otherwise:

As used herein, the term "a cell population enriched for hematopoietic stem cells" refers to a cell population obtained using the positive and negative selection techniques described herein, wherein the hematopoietic stem cells are LTR- or STR-HSCs.

As used herein, the terms "HSC expansion" and an "increased number of HSC" refer to an increase in the number of LTR-HSC and STR-HSC.

As used herein, the terms "stem cell expansion" and an "increased number of stem cells" refer to an increase in the number of stem cells which are not necessarily HSC.

As used herein, "long term repopulating hematopoietic stem cells" or "LTR-HSC", refers to hematopoietic stem cells that are transplantable, and contribute to all lineages of hematopoietic cells for an undefined period of time, when transplanted into totally immunosuppressed recipients and do not undergo clonal extinction, as exemplified herein by murine LTR-HSC. The long term repopulating ability of candidate hematopoietic stem cells may be evaluated in an in vivo sheep model or an in vivo NOD-SCID mouse model for human HSC and normal immunosupressed mice for murine HSC, respectively, as further described herein.

LTR-HSC have been isolated and characterized in mice using fluorescence-activated cell sorter (FACS) selection of density gradient-enriched, lineage-depleted bone marrow cells which are negative for expression of the CD34 antigen, positive for expression of the CD117 (c-kit) antigen, and exhibit low-level binding of the DNA binding dye, Hoechst 33342 (Ho-33342) and the mitochondrial binding dye, Rhodamine 123 (Rh-123), (Wolf, et al., 1993). The isolated cell population was demonstrated to be transplantable and capable of repopulating lethally irradiated recipients, when transplanted together with unfractionated bone marrow cells.

As used herein, the term "short term repopulating hematopoietic stem cells" or "STR-HSC", refers to murine hematopoietic stem cells that are transplantable and contribute to all lineages of hematopoietic cells for a period of from about one week to 6 months, then undergo clonal extinction. The STR-HSC population may be selected by FACS sorting and are phenotypically defined as light density gradient-enriched bone marrow cells which lack the expression of lineage markers (lin-), are positive for c-kit (CD 117), Sca1 and CD34, exhibit low-level binding of the DNA binding dye, Hoechst 33342 (Ho-33342) and high-level binding of the mitochondrial binding dye, Rhodamine 123 (Rh-123).

The term "clonal extinction", as used herein refers to the terminal differentiation of a single hematopoietic stem cell and all the progeny produced by clonal expansion of that cell, such that no more daughter cells are produced from the initial clone.

The term "pluripotent hematopoietic stem cells" refers to hematopoietic stem cells, capable of differentiating into all the possible cell lineages.

As used herein, the term "high proliferative potential colony forming cells" or "HPP-CFCs", as used herein relative to hematopoietic stem cells refers to murine or human cells that proliferate in response various cytokines and other culture conditions. By way of example, murine HPP-CFC are produced by culture of murine HSC in the presence of rat rSCF, mouse rIL-3 and human rIL-6. The cells proliferate in semi-solid media, such as agar or methyl cellulose or as single cells in liquid culture, and form macroclones which have a diameter greater than 1 mm, generally having greater than 100,000 cells per clone with dense multicentric centers. This population includes all murine HSCs, however, not all HPP-CFC are HSCs, and the HPP-CFC assay is not a specific assay for LTR-HSC. In contrast, low proliferative potential (LPP) clones contain from 2 to 100,000 cells per clone.

As used herein, "lineage-committed hematopoietic stem cells" are hematopoietic stem cells that have differentiated sufficiently to be committed to one or more particular cell lineages, but not all cell lineages.

As used herein, the term "lin-" or "lineage-depleted", refers to a cell population which lacks expression of cell surface antigens specific to T-cells, B-cells, neutrophils, monocytes and erythroid cells, and does not express antigens recognized by the "YW 25.12.7" antibody. (See, e.g., Bertoncello et al., 1991.)

As used herein, the terms "develop", "differentiate" and "mature" are used interchangeably and refer to the progression of a cell from a stage of having the potential to differentiate into multiple cellular lineages to becoming a more specialized cell committed to one or more defined lineages.

As used herein, the term "purified", relative to hematopoietic stem cells refers to HSCs that have been enriched (isolated or purified) relative to some or all of the other types of cells with which they are normally found in a particular tissue in nature, e.g., bone marrow or peripheral blood. In general, a "purified" population of HSCs has been subjected to density gradient fractionation, lineage depletion and positive selection for c-kit and Sca-1 expression in addition to low level staining with both Hoechst 33342 and Rhodamine 123.

As used herein, a population of cells is considered to be "enriched" for human HSC if greater than 0.1% of the CD 34+ cells have an immunophenotype characteristic of human HSC, e.g., CD34+ CD38– KDR+; or CD34+ Thy1+.

As used herein, the term "hematopoietic cells", refers to the types of cells found in the peripheral blood which are typically assayed as indicators of hematopoietic reconstitution, including platelets, neutrophils, B lymphocytes and T lymphocytes.

As used herein, the term "enriching for the human stem cells in said population" generally means increasing the percentage of human hematopoietic stem cells in the population where the HSC are characterized as positive for CD 34 and KDR and negative for cell surface expression of CD38 or positive for cell surface expression of both CD 34 and Thy1.

As used herein, the terms "compound", "agent", "oligomer" and "oligonucleotide" may be used interchangeably with respect to the antisense oligonucleotides of the invention. Similarly, the terms "compound" and "agent" may be used interchangeably with respect to the chemotherapeutic compounds for use in practicing the invention.

As used herein, the terms "antisense oligonucleotide" and "antisense oligomer" are used interchangeably and refer to a sequence of nucleotide bases and a subunit-to-subunit backbone that allows the antisense oligonucleotide or oligomer to hybridize to a target sequence in an RNA by Watson-Crick base pairing, to form an RNA:oligomer heteroduplex within the target sequence. The oligomer may have exact sequence complementarity to the target sequence or near complementarity. Such antisense oligomers may block or inhibit translation of the mRNA containing the target sequence, or inhibit gene transcription, may bind to double-stranded or single stranded sequences, and may be said to be "directed to" a sequence with which it hybridizes.

Exemplary structures for antisense oligonucleotides for use in the invention include the β-morpholino subunit types shown in FIGS. 1A–D. It will be appreciated that a polymer may contain more than one linkage type.

As used herein, a "morpholino oligomer" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen.

Figure 2A:
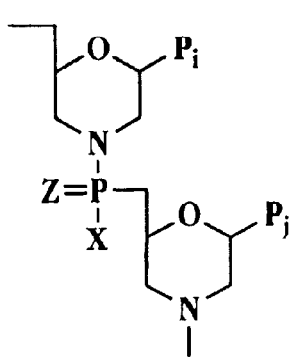
FIGS. 2A–D show the repeating subunit segment of exemplary morpholino oligonucleotides, designated A through D, constructed using subunits A–D, respectively, of FIG. 1.
Figure 2B:
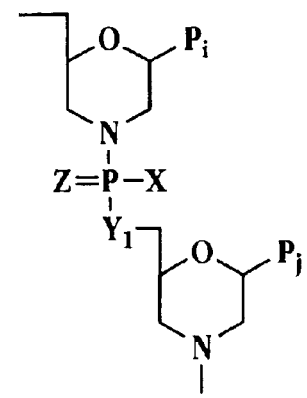

A preferred "morpholino" oligonucleotide is composed of morpholino subunit structures of the form shown in FIG. 2B, where (i) the structures are linked together by phosphorous-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. This preferred phosphorodiamidate morpholino oligomer is also referred to by the term "PMO".

As used herein, a "nuclease-resistant" oligomer is one with a backbone that is not susceptible to nuclease cleavage of a phosphodiester bond. Exemplary nuclease resistant antisense oligomers are oligonucleotide analogs, such as phosphorothioate and phosphate-amine DNA (pnDNA), both of which have a charged backbone, and methylphosphonate, morpholino, and peptide nucleic acid (PNA) oligonucleotides, all of which have uncharged backbones.

As used herein, an oligonucleotide or antisense oligomer "specifically hybridizes" to a target polynucleotide if the oligomer hybridizes to the target under physiological conditions, with a Tm substantially greater than 37° C., preferably at least 50° C., and typically 60° C.–80° C. or higher. Such hybridization preferably corresponds to stringent hybridization conditions, selected to be about 10° C., and preferably about 5° C. lower than the thermal melting point ($T_{[m]}$) for the specific sequence at a defined ionic strength and pH. At a given ionic strength and pH, the $T_{[m]}$ is the temperature at which 50% of a target sequence hybridizes to a complementary polynucleotide.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules.

As used herein the term "analog" with reference to an oligomer means a substance possessing both structural and chemical properties similar to those of the reference oligomer.

As used herein, a first sequence is an "antisense sequence" with respect to a second sequence if a polynucleotide whose sequence is the first sequence specifically binds to, or specifically hybridizes with, the second polynucleotide sequence under physiological or in vitro culture conditions.

As used herein, a "base-specific intracellular binding event" refers to the specific binding of an oligomer with a target RNA sequence inside a cell. The base specificity of such binding is sequence specific. For example, a single-stranded polynucleotide can specifically bind to a single-stranded polynucleotide that is complementary in sequence.

As used herein, "nuclease-resistant heteroduplex" refers to a heteroduplex formed by the binding of an antisense oligomer to its complementary target, which is resistant to in vivo degradation by ubiquitous intracellular and extracellular nucleases.

As used herein, the term "target", relative to an mRNA or other nucleic acid sequence, refers to an mRNA or other nucleic acid sequence which is preferentially expressed in hematopoietic stem cells. Preferentially expressed means the target mRNA is derived from a gene expressed in hematopoietic stem cells to a greater extent than the same gene is expressed in more differentiated cells, or expression specific to hematopoietic stem cells and not detectable in more differentiated cells.

As used herein, the term "modulating expression" relative to oligonucleotides refers to the ability of an antisense oligomer to either enhance or reduce the expression of a given protein by interfering with the expression, or translation of RNA. In the case of enhanced protein expression, the antisense oligomer may block expression of a suppressor gene, e.g., a tumor suppressor gene or induce upregulation of the transcription of TGF-β. In the case of reduced protein expression, the antisense oligomer may directly block expression of a given gene, or contribute to the accelerated breakdown of the RNA transcribed from that gene.

As used herein, the term "biological effect of TGF-β on stem cells" refers to the inhibition of the initial cell divisions of long-term repopulating hematopoietic stem cells and/or modulation of the rate of cellular differentiation by TGF-β. It follows that factors involved in inactivating TGF-β itself or in inactivating factors in the TGF-β receptor signaling pathway may be used to block the biological effect of TGF-β on stem cells.

As used herein, the term "TGF-β blocking agent" includes oligomers antisense to TGF-β, oligomers antisense to a factor involved in TGF-β expression or downstream signaling, a human monoclonal antibody specifically immunoreactive with TGF-β, a human monoclonal antibody specifically immunoreactive with a factor involved in activation of latent TGF-β, or naturally occurring mediators that inhibit the activity of TGF-β, such as Decorin, a chondroitin-dermatan sulfate proteoglycan found in the extracellular matrix.

As used herein, the term "culture conditions that facilitate expansion and differentiation of the stem cells" relative to a TGF-β blocking agent-treated stem cell population is exemplifed by a cell culture comprising fibroblasts, endothelial cells and megakaryocytes plus thrombopoietin and IL-6.

As used herein, the term "preserve the viability and differentiation state of said stem cells" relative to culture of a cell population comprising HSC refers to maintaining a cell viability of at least 80%, preferably a cell viability of at least 85% and more preferably a cell viability of at least 90%, as determined by an assay for cell viability routinely used by those of skill in the art, e.g., a propidium iodide assay, by an in vitro culture assay in medium containing exogenously provided cytokines, or by transfer to an in vivo model for long term reconstitution, e.g., an in vivo sheep model or in vivo NOD-SCID mouse model for human HSC, or a model for long-term reconstitution of mice with murine HSC, as further described below. With regard, preserving the differentiation state of "said stem cells", the term means maintenance of HSC having the same differentiation state as the cells used to initiate the culture, e.g., an immunophenotype characteristic of human HSC, for example, CD34+ CD38– KDR+; or CD34+ Thy1+.

As used herein, the terms "in vivo repopulation" and "in vivo reconstitution" relative to stem cell transplantation or culture in vitro generally refers to repopulation of all of the hematopoietic lineages in the subject. It follows that "time to repopulation" and "time to reconstitution" refer to the amount of time following in vivo administration of a stem cell composition until the time that the absolute count of a given cell type in the peripheral blood reaches a number of cells accepted by those of skill in the art as within the normal range for the subject.

When the term "in vivo repopulation" and "in vivo reconstitution" is used relative to neutrophils or platelets, it generally refers to an absolute neutrophil count in the peripheral blood which is greater than 500/µl or an absolute platelet count which is greater than 30,000/µl. Hence, for neutrophils or platelets, the "time to repopulation" and "time to reconstitution" refer to the amount of time following in vivo administration of a stem cell composition until the time that the absolute neutrophil count in the peripheral blood is greater than 500/µl or the absolute platelet count is greater than 30,000 µl.

As used herein, the terms "tumor" and "cancer" refer to a cell that exhibits a loss of growth control and forms unusually large clones of cells. Tumor or cancer cells generally have lost contact inhibition and may be invasive and/or have the ability to metastasize.

As used herein, "effective amount" relative to an antisense oligomer refers to the amount of antisense oligomer administered to a mammalian subject, either as a single dose or as part of a series of doses, that is effective to inhibit expression of a selected target nucleic acid sequence. As used herein "treatment" of an individual or a cell is any type of intervention used in an attempt to alter the natural course of the individual or cell. Treatment includes, but is not limited to, administration of e.g., a pharmaceutical composition, and may be performed either prophylactically, or subsequent to the initiation of a pathologic event or contact with an etiologic agent.

As used herein, the term "improved therapeutic outcome" relative to a cancer patient refers to a slowing or diminution of the growth of cancer cells or a solid tumor, or a reduction in the total number of cancer cells or total tumor burden.

II. Hematopoietic Stem Cell Methods and Compositions

The present invention is directed to methods and compositions effective to block the biological effect of TGF-β on hematopoietic stem cells. It will be understood that such blocking may be accomplished using any of a number of methods, e.g., an oligomer antisense to TGF-β; an oligomer antisense to a factor involved in TGF-β upregulation or downstream signaling of the TGF-β receptor, e.g., TGF-β signal transduction; a human monoclonal antibody specifically immunoreactive with TGF-β; or a human monoclonal antibody specifically immunoreactive with a factor involved in TGF-β activation or signaling. Exemplary cell surface factors which directly inhibit TGF-β include Decorin and neutralizing monoclonal antibodies. By way of example, the biological effect of TGF-β on stem cells may be inhibited by antisense oligomers specific to TGF-P ligand, tissue transglutaminase, type I and type II TGF-β receptor subunits, Smad 2&3, Rb-1, p21 and p27 signaling components.

In order to effectively block the effect of TGF-P on stem cells, the agent (antisense oligomer or antibody) must be specific for TGF-β, preferably TGF-β1 or TGF-β2, and have the ability to modify stem cells following short term exposure of the cells to the agent in the absence of exogenously provided cytokines. Treatment of stem cells with such an agent is effective to (1) prolong stem cell survival in vitro at 37° C. or 4° C.; (2) promote rapid hematopoietic repopulation following in vivo administration of treated stem cells; (3) induce sustained repopulation following in vivo administration; (4) induce rapid stem cell proliferation in vitro following transfer to culture conditions effective to promote such proliferation; (5) induce stem cell proliferation in vitro with a minimal number of cells; and (6) provide for sustained stem cell proliferation in vitro resulting in generation of various lineages of hematopoietic cells.

Upon treatment with such an agent, e.g. an oligomer antisense to TGF-β, treated stem cells maintain the ability to provide long term sustained hematopoietic reconstitution (in vitro and in vivo), and also exhibit the capability of short term in vitro and in vivo repopulation, a quality which untreated stem cells do not possess.

It will be understood that any agent which exhibits the above-described characteristics finds utility in the methods and compositions of the invention and that the invention is not limited to the specific agents included in the examples described herein.

III. TGF-β1 and Hematopoietic Stem Cells

TGF-β1 has been shown to directly and reversibly inhibit the initial cell divisions of long-term repopulating hematopoietic stem cells (LTR-HSC) in vitro. See, e.g., Sitnicka et al, 1996 and Ploemacher et al., 1993; Ottmann et al., 1988; and Cashman et al., 1990.

It follows that blocking the effects of TGF-β would be expected to promote such initial cell divisions. However, the various literature references directed to the effect of TGF-β and anti-TGF-β antibodies on HSC do not provide consistent results. For example, the administration of TGF-β to humans has been described as capable of enhancing the number of hematopoietic progenitor cells in the peripheral blood. (See, e.g. U.S. Pat. No. 5,674,843, issued Oct. 7, 1997) In other references the effect of TGF-β on stem and progenitor cells has been described as inhibition of cell proliferation or mediation of apoptosis, based on the demonstration that LTR-HSC cultured with greater than 0.1 ng/ml TGF-β1 (plus hematopoietic growth factors [HGF]), increased the probability of the maintenance or expansion of HPP daughter cells (Sitnicka et al, 1996).

Greater than 90% of single sorted murine LTR-HSC (lineage neg., Rh$^{low}$, Ho$^{low}$, c-kit+, Sca-1+) have been shown to form high proliferative potential (HPP) clones in the presence of SCF, IL-3, and IL-6 (Sitnicka et al., 1996). In addition, such studies have indicated that essentially 100% of purified HSC cultured as single cells undergo their first cell division if specific hematopoietic cytokine combinations are present, e.g., SCF (c-kit ligand) plus IL-6, IL-11, IL-12, or IL-3 (Sitnicka et al. 1996).

LTR-HSC have also been shown to express either an active cell surface form and/or an active secreted form of TGF-β1 (Lucas et al., 1990). Such endogenously expressed TGF-β1 is sufficient to arrest cell division if cultured in the presence of single growth factors that have been identified as survival factors for single LTR-HSC (Li et al., 1994; Ploemacher et al., 1993). In addition, greater than 90% of LTR-HSC clones exhibited a high proliferative potential (HPP), which is defined as clones able to attain greater than 100,000 cells by day 14 of culture in response to SCF, IL-6 and IL-3; and are generally characterized by: (1) a relative resistance to treatment in vivo with the cytotoxic drug 5-fluorouracil; (2) a high correlation with cells capable of repopulating the bone marrow of lethally irradiated mice; (3) the ability to generate cells of the macrophage, granulocyte, megakaryocyte and erythroid lineages, and (4) the multifactor responsiveness. (See, e.g., McNiece, I. K., 1990).

It has been demonstrated that LTR-HSC do not survive in culture without cell division and/or differentiation and that the survival of single LTR-HSC cultured in medium which lacks exogenously provided cytokines, is limited to a few days.

Human adult hematopoietic stem cells are mostly quiescent or slow cycling. However, the results presented herein demonstrate that when human hematopoietic stem cells are cultured under conditions which lack exogenously provided cytokines, wherein TGF-β is blocked, quiescent, hematopoietic multipotent progenitors grow in a short term culture assay in which the cells do not grow without blocking TGF-β.

The results presented herein demonstrate that treatment of LTR-HSC with a morpholino oligomer antisense to the Type II TGF-β receptor results in survival of LTR-HSC for at least 5 days, while untreated and control-treated HSC do not survive. (See Example 1.) Additional studies have shown that treatment of LTR-HSC with a PMO antisense to TGF-β results in survival of murine LTR-HSC for at least 18 days prior to transfer to an in vitro assay in medium containing exogenously provided cytokines or to an in vivo reconstitution model (further described below).

The results presented herein also demonstrate that exposure of LTR-HSC to an oligomer antisense to TGF-β for as short a time as from 4 to 24 hours, followed by transfer into lethally irradiated mice, is effective promote both rapid and long term repopulation of the hematopoietic system of the mice. (See Example 2.)

IV. Antisense Oligomers

There are numerous references to the use of antisense oligonucleotides or antibodies to specifically interfere with synthesis of a target protein of interest. Due to their hydrophobicity, antisense oligonucleotides interact well with phospholipid membranes (Akhtar et al., 1991), and it has been suggested that following the interaction with the cellular plasma membrane, oligonucleotides are actively transported into living cells (Loke et al., 1989; Yakubov et al., 1989; Anderson et al., 1999).

Antisense oligonucleotides for use in practicing the present invention comprise nucleotide subunits joined by internucleotide backbone linkages which present the nucleotide bases for hybridization with target nucleic acid sequences. Antisense oligomers are useful to control gene expression through complementary polynucleotides, e.g., DNA or RNA antisense to the control, 5' or regulatory regions of the target gene. In some cases, such antisense oligonucleotides may target a splice junction in the target mRNA.

Antisense oligonucleotides of 15–20 bases are generally long enough to have one complementary sequence in the mammalian genome. In addition, antisense compounds having a length of at least 17 nucleotides in length hybridize well with their target mRNA (Cohen, et al., 1991). Due to their hydrophobicity, antisense oligonucleotides interact well with phospholipid membranes (Akhtar, et al., 1991), and it has been suggested that following the interaction with the cellular plasma membrane, oligonucleotides are actively transported into living cells (Loke, et al., 1989; Yakubov, et al., 1989; Anderson, et al., 1999).

Morpholino oligonucleotides, particularly phosphoramidate- or phosphorodiamidate-linked morpholino oligonucleotides have been shown to have high binding affinities for complementary or near-complementary nucleic acids. Morpholino oligomers also exhibit little or no non-specific antisense activity, afford good water solubility, are immune to nucleases, and are designed to have low production costs (Summerton et al., 1997).

Morpholino oligonucleotides (including antisense oligomers) are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein In one preferred approach, antisense oligomers for use in practicing the invention are composed of morpholino subunits of the form shown in the above cited patents, where (i) the morpholino groups are linked together by uncharged linkages, one to three atoms long, joining the morpholino nitrogen of one subunit to the 5' exocyclic carbon of an adjacent subunit, and (ii) the base attached to the morpholino group is a purine or pyrimidine base-pairing moiety effective to bind, by base-specific hydrogen bonding, to a base in a polynucleotide. The purine or pyrimidine base-pairing moiety is typically adenine, cytosine, guanine, uracil or thymine. Preparation of such oligomers is described in detail in U.S. Pat. No. 5,185,444 (Summerton et al., 1993), which is hereby incorporated by reference in its entirety. As shown in this reference, several types of nonionic linkages may be used to construct a morpholino backbone.

Exemplary backbone structures for antisense oligonucleotides of the invention include the morpholino subunit types shown in FIGS. 1A–D, each linked by an uncharged, phosphorous-containing subunit linkage. In these figures, and in FIGS. 2A–D, the X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures. Alkyl, alkoxy and thioalkoxy preferably include 1–6 carbon atoms, and more preferably 1–4 carbon atoms. Monosubstituted or disubstituted nitrogen preferably refers to lower alkyl substitution, and the cyclic structures are preferably 5- to 7-membered nitrogen heterocycles optionally containing 1–2 additional heteroatoms selected from oxygen, nitrogen, and sulfur. Z is sulfur or oxygen, and is preferably oxygen.

FIG. 1A shows a phosphorous-containing linkage which forms the five atom repeating-unit backbone shown in FIG. 2A, where the morpholino rings are linked by a 1-atom phosphoamide linkage.

Figure 1B:
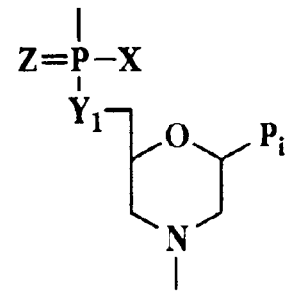

Subunit B in FIG. 1B is designed for 6-atom repeating-unit backbones, as shown in FIG. 2B. In FIG. 1B, the atom Y linking the 5' morpholino carbon to the phosphorous group may be sulfur, nitrogen, carbon or, preferably, oxygen. The X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures. Z is sulfur or oxygen, and is preferably oxygen. Particularly preferred morpholino oligonucleotides include those composed of morpholino subunit structures of the form shown in FIG. 2B, where X=NH$_2$ or N(CH$_3$)$_2$, Y=O, and Z=O.

Figure 1C:
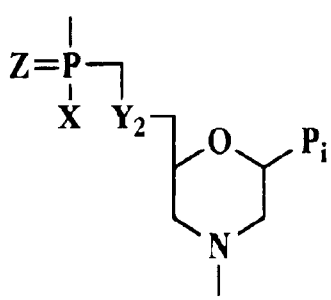
Figure 1D:
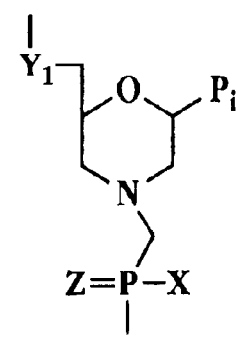
Figure 2C:
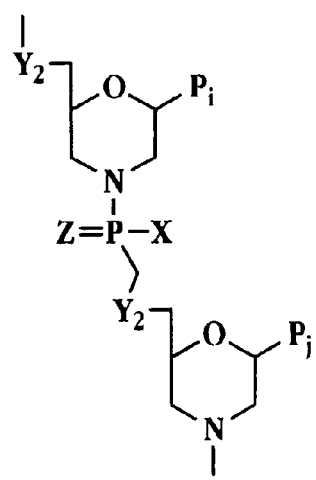
Figure 2D:
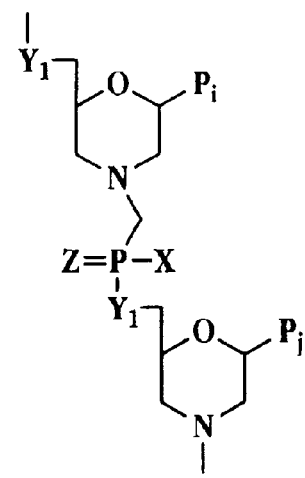

Subunits C–D in FIGS. 1C–D are designed for 7-atom unit-length backbones as shown for structures in FIGS. 2C and D. In Structure C, the X moiety is as in Structure B, and the moiety Y may be methylene, sulfur, or preferably oxygen. In Structure D, the X and Y moieties are as in Structure B. In all subunits depicted in FIGS. 1 and 2, each Pi and Pj is a purine or pyrimidine base-pairing moiety effective to bind, by base-specific hydrogen bonding, to a base in a polynucleotide, and is preferably selected from adenine, cytosine, guanine and uracil.

As noted above, the substantially uncharged oligomer may advantageously include a limited number of charged linkages, e.g. up to about 1 per every 5 uncharged linkages. In the case of the morpholino oligomers, such a charged linkage may be a linkage as represented by any of FIGS. 2A–D, preferably FIG. 2B, where X is oxide (—O$^-$) or sulfide (—S$^-$).

Figure 3A:
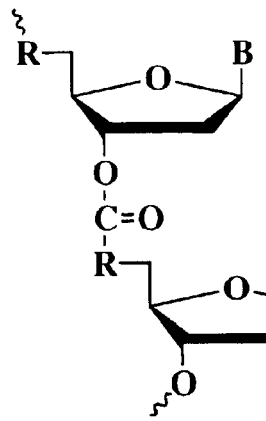
FIGS. 3A–3G show examples of uncharged linkage types in oligonucleotide analogs.
Figure 3B:
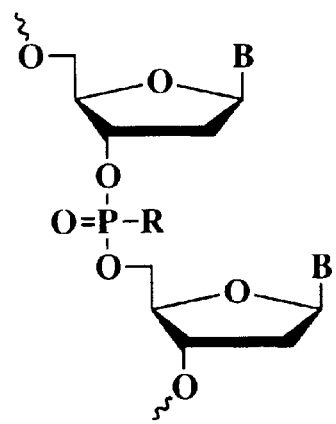
Figure 3C:
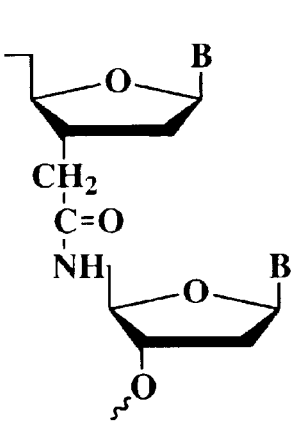
Figure 3D:
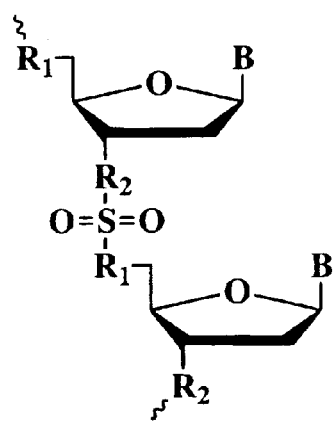
Figure 3E:
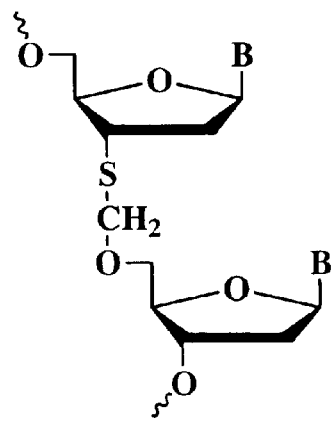
Figure 3F:
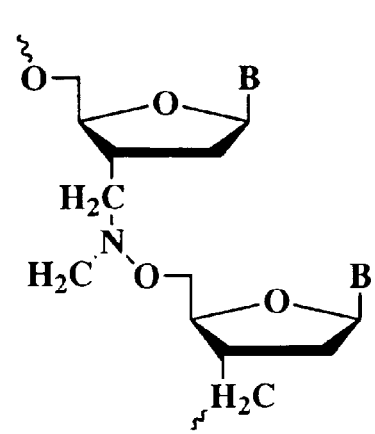
Figure 3G:
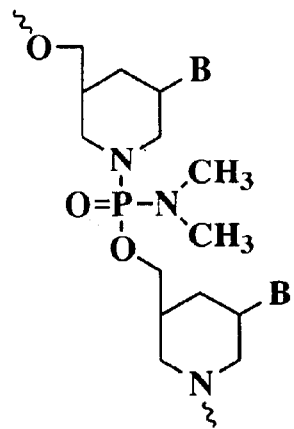

Especially preferred is a substantially uncharged morpholino oligomer such as illustrated by the phosphorodiamidate morpholino oligomer (PMO) shown in FIG. 3G.

In the methods of the invention, the antisense oligomer is designed to hybridize to a region of the target nucleic acid sequence, under physiological conditions with a Tm substantially greater than 37° C., e.g., at least 50° C. and preferably 60° C.–80° C., wherein the target nucleic acid sequence is preferentially expressed in hematopoietic stem cells. The oligomer is designed to have high-binding affinity to the target nucleic acid sequence and may be 100% complementary thereto, or may include mismatches, e.g., to accommodate allelic variants, as long as the heteroduplex formed between the oligomer and the target nucleic acid sequence is sufficiently stable to withstand the action of cellular nucleases and other modes of degradation during its transit from cell to body fluid. Mismatches, if present, are less destabilizing toward the end regions of the hybrid duplex than in the middle. The number of mismatches allowed will depend on the length of the oligomer, the percentage of G:C base pair in the duplex and the position of the mismatch(es) in the duplex, according to well understood principles of duplex stability.

Although such an antisense oligomer is not necessarily 100% complementary to a nucleic acid sequence that is preferentially expressed in hematopoietic stem cells, it is effective to stably and specifically bind to the target sequence such that expression of the target sequence is modulated. The appropriate length of the oligomer to allow stable, effective binding combined with good specificity is about 8–40 nucleotide base units, and preferably about 12–25 nucleotides. Oligomer bases that allow degenerate base pairing with target bases are also contemplated, assuming base-pair specificity with the target is maintained.

mRNA transcribed from the relevant region of a gene associated with TGF-β expression is generally targeted by the antisense oligonucleotides for use in practicing the invention, however, in some cases double-stranded DNA may be targeted using a non-ionic probe designed for sequence-specific binding to major-groove sites in duplex DNA. Such probe types are described in U.S. Pat. No. 5,166,315 (Summerton et al., 1992), which is hereby incorporated by reference, and are generally referred to herein as antisense oligomers, referring to their ability to block expression of target genes.

In one preferred approach, an antisense oligonucleotide directed to the start site, e.g. between positions −10 and +10, of the translational start site of a gene product associated with TGF-β expression, is provided, where the antisense oligonucleotide is designed to interfere with, or prevent, transcription and the subsequent expression of TGF-β. [See, e.g., Lee et al., 1979; Cooney et al., 1988; and Dervan et al., 1991].

In one aspect of the invention, an antisense oligonucleotide effective to block the expression of TGF-β, preferably an uncharged PMO antisense finds utility in practicing the invention. In another aspect, the antisense oligonucleotide is a PMO directed to a region spanning the start codon of an mRNA specific to a factor involved in TGF-β signal transduction, e.g., Vla-4, tissue transglutaminase, type I or type II TGF-β receptor subunits, Smad 2&3, Rb-1, p21 or a p27 signaling components. Alternatively, the splice acceptor region of an mRNA associated with TGF-β expression is targeted by a PMO for use in practicing the invention.

Antisense oligomers for use in practicing the invention, preferably have one or more properties including: (1) a backbone that is substantially uncharged (e.g., Uhlmann, et al., 1990), (2) the ability to hybridize with the complementary sequence of a target RNA with high affinity, that is a Tm substantially greater than 37° C., preferably at least 50° C., and typically 60° C.–80° C. or higher, (3) a subunit length of at least 8 bases, generally about 8–40 bases, preferably 12–25 bases, (4) nuclease resistance (Hudziak, et al., 1996) and (5) capability for active or facilitated transport as evidenced by (i) competitive binding with a phosphorothioate antisense oligomer, and/or (ii) the ability to transport a detectable reporter into cells.

In general, the target for modulation of gene expression comprises a sequence spanning the mRNA translational start codon of the mRNA which encodes TGF-β. However, in some cases, other regions of the TGF-β mRNA may be targeted, including one or more of, an initiator or promoter site, an intron or exon junction site, a 3'-untranslated region, and a 5'-untranslated region. In addition, both spliced and unspliced RNA may serve as the template for design of antisense oligomers for use in the methods of the invention. In some cases a splice junction of TGF-β mRNA is targeted. In other cases, an mRNA for a factor involved in the TGF-β receptor signaling pathway is targeted, examples of which include RB protein, vla4, tissue transglutaminase, type I and type II TGF-β receptor subunits, Smad 2&3, Rb-1, p21 and p27.

Exemplary antisense oligomers for use in practicing the invention include the sequences presented as SEQ ID NO:1, SEQ ID NO:2 and SEQ ID NO:5.

The antisense compounds for use in practicing the invention can be synthesized by stepwise solid-phase synthesis, employing methods detailed in the references cited above. The sequence of subunit additions will be determined by the selected base sequence. In some cases, it may be desirable to add additional chemical moieties to the oligomer compounds, e.g. to enhance the pharmacokinetics of the compound or to facilitate capture or detection of the compound. Such a moiety may be covalently attached, typically to the 5'- or 3'-end of the oligomer, according to standard synthesis methods. For example, addition of a polyethyleneglycol moiety or other hydrophilic polymer, e.g., one having 10–100 polymer subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an oligomer antisense, it is generally of course desirable to select chemical compounds of groups that are biocompatible and likely to be tolerated by cells in vitro or in vivo without undesirable side effects.

A. Evaluation of Candidate Antisense Oligomers

Candidate antisense oligomers may be evaluated, according to well known methods, for acute and chronic cellular toxicity, such as the effect on protein and DNA synthesis as measured via incorporation of $^3$H-leucine and $^3$H-thymidine, respectively. In addition, various control oligonucleotides, e.g., control oligonucleotides such as sense, nonsense or scrambled antisense sequences, or sequences containing mismatched bases, in order to confirm the specificity of binding of candidate antisense oligomers. The outcome of such tests are important to discern specific effects of antisense inhibition of gene expression from indiscriminate suppression. (See, e.g. Bennett et al., 1995). Accordingly, sequences may be modified as needed to limit non-specific binding of antisense oligomers to non-target nucleic acid sequences.

The effectiveness of a given antisense oligomer molecule in forming a heteroduplex with the target mRNA may be determined by screening methods known in the art. For example, the oligomer is incubated a cell culture containing an mRNA preferentially expressed in hematopoietic stem cells, and the effect on the target mRNA is evaluated by monitoring the presence or absence of (1) heteroduplex formation with the target sequence and non-target sequences using procedures known to those of skill in the art, (2) the amount of the target mRNA which expressed by hematopoietic stem cells, as determined by standard techniques such as RT-PCR or Northern blot, or (3) the amount of protein transcribed from the target mRNA, as determined by standard techniques such as ELISA or Western blotting. (See, for example, Pari et al., 1995; Anderson et al., 1996).

More specific evaluation is carried out using in vitro assays with cell populations enriched for HSC, where the cells are cultured in the presence of various antisense oligomers and evaluated for maintenance of the viability and differentiation state of the HSC.

In one exemplary approach, a cell population enriched for HSC is prepared from mobilized human peripheral blood and placed in culture in medium which lacks exogenously provided cytokines, with some assay conditions including PMOs specific for a sequence which encodes TGF-β or a factor involved in TGF-β signal transduction, together with various PMO and medium controls. After from 4 to 24 hours exposure to the antisense oligomers, the culture is evaluated for viable HSC and/or the HSC are transferred to culture medium containing a mixture of cytokines which allows the HSC to differentiate to lineage committed progenitor cells and their progeny.

In one exemplary approach, the TGF-β blocking agent-treated HSC are cultured in medium containing stem cell factor (SCF) at a final concentration of 50 ng/ml, together with 20 ng/ml IL-6 and 50 ng/ml IL-3, such that cells which divide one or more times over 7 days in the presence of the growth factors are considered to be viable at the time of growth factor addition.

V. Anti TGF-β Antibodies and Stem Cells

A number of different types of cells have been shown to express TGF-β. TGF-β expression has been associated with differentiating cells, bone marrow and fetal liver progenitor cells in experiments using antibodies to TGF-β (Ellingsworth et al, 1986). Two forms of TGF-β were distinguished by multipotential hematopoietic progenitor cells and TGF-β1 (but not TGF-β2) has been shown to inhibit hematopoietic progenitor cells (Ohta et al., 1987).

In one report, purified human umbilical cord blood CD34+ cells were fractionated into CD38+ and CD38− cells then treated with either an anti-TGF-β antibody or a phosphorothioate oligonucleotide antisense to TGF-β. It was demonstrated that more differentiated CD34+38+ cells were less sensitive to anti TGF-P treatment than the more immature CD34+38− cells (Cardoso et al., 1993).

Various references to culture of hematopoietic cells in the presence of anti TGF-β antibodies may be found in the literature. The recited culture conditions vary considerably, however, in general the references describe bone marrow cells or stem cell-enriched cell preparations cultured under conditions which include combinations of cytokines.

The release of CD34 positive human hematopoietic progenitor cells from quiescence has been reported following treatment with a phosphorothioate antisense oligomer to TGF-β1 or Rb1 in culture medium in the presence of exogenously provided cytokines, e.g., IL3, IL6, IL11, steel factor, (SF), G-CSF, GM-CSF and EPO (Hatzfeld et al., 1991; Fortunel et al., 1998).

In one literature report, TGF-β was added to ex vivo cultures of murine stem cells containing interleukin-3 (IL-3), IL-6, and stem cell factor (SCF) and was shown to suppress short- and long-term repopulating activity of the cells in a murine competitive repopulation assay. An anti TGF-β neutralizing antibody, reversed such effects relative to control cultures containing IL-3, IL-6, and SCF alone (Soma et al., 1996).

Several other references describe murine marrow cells treated with an oligomer antisense to TGF-beta together with various cytokines, e.g., IL-3, IL-6 and stem cell factor, wherein a greater retroviral transduction efficiency was observed in progenitor (CFU-C) and long-term repopulating cells relative to cells treated with IL-3, IL-6 and stem cell factor alone. (See, e.g., Yu J et al., 1998).

In another example, Dexter-type long-term murine bone-marrow cultures were treated with a monoclonal antibody that neutralizes the biological activity of TGF-β resulting in at least three times as many stem cells as control cultures (Waegell et al., 1994).

Improved gene transfer into human hematopoietic progenitor cells prestimulated with cytokines was demonstrated when the effect of TGF-β1 was blocked by antisense or antiserum to release stem cells from quiescence. (See, e.g., Hatzfeld et al., 1991, Imbert et al., 1998; and U.S. Pat. No. 5,958,774.)

Such experiments are generally directed to releasing stem cells from quiescence (ie., causing them to enter the cell cycle and to differentiate).

Numerous anti TGF-β antibodies are described in the literature and many are commercially available. Exemplary anti TGF-β antibodies include the following murine monoclonal antibodies: (1) ID11.16, prepared by immunization with bovine TGF-β2; (2) 12H5, prepared by immunization with human TGF-pl; (3) 2G7, prepared by immunization with human TGF-β1; and (4) 3C7.14, prepared by immunization with human TGF-β2.

Of particular interest in practicing the methods described herein are human monoclonal antibodies specifically immunoreactive with TGF-β, preferably human monoclonal antibodies specifically immunoreactive with human TGF-β which block the biological effects of TGF-β on HSC.

In one preferred approach, transgenic animals (e.g. xenomice) may be produced which are capable, upon immunization, of producing a full repertoire of human antibodies in the absence of endogenous immunoglobulin production. In this approach, large fragments of both the human heavy and light chain Ig genes have been inserted into the mouse germine to create a mouse strain capable of producing a broad repertoire of antigen-specific, fully human antibodies.

The xenomouse produces B cells expressing human heavy chain (h mu) and human K light chain (h K), or h mu and mouse lambda (m lambda) light chain. These mice produce significant quantities of fully human antibodies with a diverse adult-like repertoire and, upon immunization with antigens, generate antigen-specific fully human monoclonal antibodies. (See, e.g., Jakobovits, et al., 1995; Jakobovits, A, 1995.

Such xenogenic mouse-derived human monoclonal antibodies may not have the correct Ig heavy chain for complement fixation in humans, e.g., IgG1. In such cases, the antibody encoding mRNA from the xenogenic mouse hybridoma may be used to obtain cDNA into which the appropriate cDNA for the IgG1 heavy chain is inserted. This cassette may then be inserted into an expression vector using procedures routinely employed by those of skill in the art, and subsequently for used in the production of transgenic goats. Transgenic goats have been developed wherein inducible promoters can trigger the expression of the protein encoded therein such that it is secreted into the milk of the goats. This procedure allows for relatively low cost production of large quantities of human monoclonal antibodies.

VI. Hematopoietic Stem Cells

A. Methods of Obtaining Hematopoietic Stem Cells

In adults, the majority of pluripotent hematopoietic stem cells are found in the bone marrow. However, small but significant numbers of such cells can be obtained from the peripheral circulation, liver, spleen and cord blood.

Human hematopoietic stem cells for use in the present invention may be derived from human bone marrow, human newborn cord blood, fetal liver, or adult human peripheral blood after appropriate mobilization.

The frequency of hematopoietic stem cells can be dramatically increased by treatment of a subject with certain compounds including cytokines. Such "mobilized" peripheral blood hematopoietic stem cells have become an important alternative to bone marrow-derived hematopoietic stem cells transplantation procedures primarily because engraftment is more rapid. (See, e.g., Tanaka et al., 1999.)

Such mobilization may be accomplished using for example, one or more of granulocyte colony-stimulating factor (G-CSF), stem cell factor (SCF), thrombopoietin (Tpo), and a chemotherapeutic agent (i.e., cyclophosphamide).

Numerous methods for human hematopoietic stem cell enrichment/isolation are known in the art and generally include obtaining bone marrow, newborn cord blood, fetal liver or adult human peripheral blood which contains hematopoietic stem cells. Once obtained, the hematopoietic stem cell component may be enriched by performing various separation techniques such as density gradient separation, immunoaffinity purification using positive and/or negative selection by panning, FACS, or magnetic bead separation. Following such enrichment steps, the cell population is typically characterized both phenotypically and functionally.

Previous studies have also demonstrated that primitive hematopoietic cells, characterized as high proliferative potential colony-forming cells (HPP-CFC, in vitro) may be isolated by selecting a fraction of density gradient-enriched, lineage-depleted marrow cells, further selecting a cell population based on a single step fluorescence-activated cell sorter (FACS) fractionation for cells that bind low levels of the DNA binding dye, Hoechst 33342 (Hoechst$^{lo}$) and low levels of the mitochondrial binding dye, Rhodamine 123 (Rho$^{lo}$; Wolf et al., 1993.

In one exemplary enrichment method, normal murine marrow cells are processed using two pre-enrichment steps based on density gradient centrifugation (e.g., using Nycodenz 1.080 g/ml, Nygaard, Oslo, Norway), followed by negative selection using Dynal beads coupled to myeloid and lymphoid specific monoclonal antibodies and positive selection by FACS sorting of cells based on staining with Rhodamine 123 (Rh), Hoescht 3342(Ho) and antibodies to c-kit.

Once obtained, such candidate HSC may be characterized in a variety of in vitro and in vivo assays generally known in the art, as further described below. Such assays include, but are not limited to, an HPP-CFC assay, a single-cell HPP daughter cell assay, a single-cell IL-3 response assay, a single-cell assay for time to the first cell division, a cobblestone area-forming cell assay and an in vivo limiting dilution transplant assay to quantitate STR- and LTR-HSC.

Recently, it has been shown that a defined subpopulation of murine HPP-CFC are transplantable. It was further demonstrated that a subpopulation of the cells that give rise to HPP-CFC are LTR-HSCs, which can replicate ex vivo, as shown by the results of in vitro LTBMC and in vivo repopulation studies. (See, e.g., Yagi M et al., 1999).

Once a hematopoietic stem cell population is obtained, the cells may be used immediately or frozen in liquid nitrogen and stored for long periods of time, using standard conditions, such that they can later be thawed and used, e.g., for administration to a patient. The cells are typically stored in 10% DMSO, 50% fetal calf serum (FCS), and 40% cell culture medium.

B. Culture and Function of Hematopoietic Stem Cells

Hematopoietic stem cells have been historically defined as transplantable cells, capable of self-renewal which possess the ability to generate daughter cells of any hematopoietic lineage. Lineage-committed progenitor cells are defined as more differentiated cells derived from hematopoietic stem cells.

The phenotypic markers which characterize the hematopoietic stem cell have been the subject of extensive debate and numerous publications. As yet, there is no consensus as to which markers are definitive for murine or human hematopoietic stem cells, however, the markers for LTR-HSC and STR-HSC, as used herein, are provided above.

Functional readouts that have been used to detect and characterize hematopoietic stem cells include the ability to form colonies under particular conditions in cell culture (in vitro), such as in the long term culture initiating cell (LTCIC) assay (Pettengell et al., 1994), long term bone marrow culture (LTBMC; Dexter et al., 1984) and the high proliferative potential-colony-forming cell (HPP-CFC) assay. (See, e.g., Yagi et al., 1999.) Further functional characterization includes in vivo assay for long-term repopulating hematopoietic stem cells (LTR-HSC) and short-term repopulating hematopoietic stem cells (STR-HSC), as further described below.

LTBMC (Dexter T M et al., 1984) develop a complex adherent stromal layer containing a large variety of cell types, and can generate nonadherent (NA) hematopoietic cells for periods of several months. Hematopoietic stem cells are also often characterized functionally by activity in the high proliferative potential colony-forming cell (HPP-CFC) assay, as defined above.

HPP-CFC are generally characterized by: (1) a relative resistance to treatment in vivo with the cytotoxic drug 5-fluorouracil; (2) a high correlation with cells capable of repopulating the bone marrow of lethally irradiated mice; (3) their ability to generate cells of the macrophage, granulocyte, megakaryocyte and erythroid lineages, and (4) their multifactor responsiveness. (See, e.g., McNiece, 1990).

C. Cytokines and Stem Cell Culture

Extensive studies have been described wherein HSC are cultured in the presence in various combinations of cytokines as a means to increase the number of HSC. In general, such culture conditions have caused differentiation of HSC and do not result in survival or increased numbers of viable long term repopulating HSC (Li et al., 1994; Peters et al., 1996; Yonemura et al., 1996).

Recently, combinations of cytokines, including stem cell factor (SCF, or c-kit ligand), thrombopoietin (Tpo, c-mpl ligand), and the ligand for the Flt3/Flk2 receptor (FL), have been shown to act directly on HSC (Ogawa et al., 1997; Ku et al., 1996; Ramsfjell et al., 1996; Sitnicka et al., 1996; Young et al., 1996; Yoshida et al., 1997; Matsunaga et al., 1998). In addition, Tpo as a single growth factor has been demonstrated to support survival and modest proliferation of highly purified HSC in vitro (Ramsfjell et al., 1996; Sitnicka et al., 1997).

D. Human HSC

Human HSC are initially characterized by immunophenotype, e.g., as lineage negative and either (1) CD34+/Thy1+ or (2) CD 34+/CD38− cells that are also KDR+. Human HSC may also be characterized by telomere length, where cells with high proliferative capacity have longer telomeres. In general, a population of cells is considered to be enriched for human HSC if greater than 0.1% of the CD 34+ cells have the immunophenotype, CD 34+CD38− KDR+ or CD34+ Thy1.

Preferred cytokines for the culture of human hematopoietic stem cells typically include one or more of interleukin-3 (IL-3), interleukin-6 (IL-6), interleukin-11 (IL-11), interleukin-12 (IL-12), stem cell factor (SCF), fms-like tyrosine kinase-3 (flt-3), transforming growth factor-$\beta$ (TGF-$\beta$), an early acting hematopoietic factor, described, for example in WO 91/05795, and thrombopoietin (Tpo).

The long term repopulating ability of candidate hematopoietic stem cells may be evaluated in an in vivo sheep model or an in vivo NOD-SCID mouse model for human HSC.

E. Murine HSC

Preferred cytokines for the culture of murine hematopoietic stem cells include one or more of interleukin-3 (IL-3), interleukin-6 (IL-6), interleukin-11 (IL-11), interleukin-12 (IL-12), stem cell factor (SCF), fms-like tyrosine kinase-3 (flt-3), transforming growth factor-$\beta$ (TGF-$\beta$), an early acting hematopoietic factor, described, for example in WO 91/05795, and thrombopoietin (Tpo).

Long-term reconstitution of mice with murine LTR-HSCs following complete immunosuppression has been shown to require the transplantation of unfractionated bone marrow cells together with less differentiated long term repopulating cells, in order to provide initial, albeit unsustained engraftment, such that the completely immunosuppressed host may survive until the long term repopulating cells differentiate sufficiently to repopulate the host. (See, e.g., Jones et al., 1990). LTR-HSCs may take several months to effectively repopulate the hematopoietic system of the host following complete immunosuppression.

Methods have been developed to distinguish the cells of the donor and recipient in murine hematopoietic reconstitution studies, by using donor hematopoietic stem cells, congenic at the CD45 locus, defined as CD45.1 and recipient hematopoietic stem cells defined as CD45.2, such that monoclonal antibodies may be used to distinguish donor and recipient cells, i.e., by FACS analysis and/or sorting. In such detection methods, the recipient is infused with sufficient CD45.2 positive bone marrow cells to keep the mouse alive until differentiation of CD45.1 donor cells occur to an extent sufficient to repopulate the hematopoietic system of the recipient. Such methods may be used to differentiate LTR-HSC from STR-HSC and donor cells from recipient cells.

VII. Methods and Compositions of the Invention

High-dose chemotherapy and/or radiation therapy together with bone marrow transplantation or transplantation of a cell population enriched for hematopoietic stem cells are standard treatment regimens for some malignancies, including, acute lymphocytic leukemia, chronic myelogenous leukemia, neuroblastoma, lymphoma, breast cancer, colon cancer, lung cancer and myelodysplastic syndrome, as well as for other non-malignant hematopoietic diseases, e.g. thrombocytopenia. Such treatments have shown promise in effective elimination of several types of cancer, however in all cases the high doses also destroy bone marrow stem cells. In addition, bone marrow transplantation or alternatively stem cell transplantation may play a major role in the emerging field of gene therapy. A low percentage of the cells present in stem cell preparations derived from peripheral blood and/or bone marrow are capable of rapid and/or long-term hematopoietic reconstitution.

In addition, due to the lack of a culture system for in vitro or ex vivo preservation of stem cells, once obtained, stem cell preparations are typically frozen in liquid nitrogen prior to use. Upon thawing, the viability and number of stem cells is further reduced. Therefore, a need exists for a means to preserve stem cells in vitro or ex vivo following enrichment in addition to a means to facilitate rapid expansion of the cells under appropriate conditions.

Accordingly, a method to preserve or increase a population of HSC without differentiation and a cellular composition comprising such an expanded, but undifferentiated population of HSC would find utility in a variety of cellular and gene therapy applications. Once obtained, such a cellular composition may be administered in vivo to a subject such that rapid expansion of lineage committed hematopoietic progenitor cells takes place providing for rapid hematopoietic reconstitution. The cellular composition of expanded, but undifferentiated HSC may also be used for in vitro culture under conditions effective to promote expansion and/or differentiation of the cells.

For example, many cancer treatment regimens result in immunosuppression of the patient, leaving the patient unable to defend against infection. Supportive care for immunosuppression may include protective isolation of the patient, such that the patient is not exposed to infectious agents; administration of antibiotics, antiviral agents and antifungal agents; and/or periodic blood transfusions to treat anemia, thrombocytopenia (low platelet count), or neutropenia (low neutrophil count).

Current transplantation regimens that employ cell populations enriched for hematopoietic stem cells and/or bone marrow transplantation also suffer from an excessive lag time between transplantation and repopulation of the patient's hematopoietic system. In particular, such patients often suffer from a deficiency in neutrophils and platelets. Neutrophils are involved in defending the host against infection. Frequently, following a chemotherapy or radiation therapy, a patient will suffer from insufficient neutrophil counts for time period of from about 3 to 4 weeks, or a longer time period resulting in increased susceptibility to infection. Platelets are necessary for effective blood clotting at a site of injury. Frequently, following chemotherapy, radiation therapy, transplantation of a cell population enriched for hematopoietic stem cells or bone marrow transplantation, a patient will suffer from an insufficient platelet count for a time period of from about 4 to 6 weeks, or a longer time period resulting in the patient being easily bruised and excessive bleeding.

In one embodiment, the treatment of stem cells with an agent effective to block the biological activity of TGF-$\beta$, e.g., an antisense oligomer to TGF-$\beta$, provides a means to maintain cells having the phenotype and function of stem cells for an extended time in culture (at 37° C. or 4° C.) without cell division or differentiation.

In a related embodiment, these cells serve as a cellular source for the rapid and sustained repopulation of the hematopoietic system of a host following in vivo administration of the treated stem cells. Alternatively, the treated stem cells may serve as a cellular source for rapid expansion and differentiation of stem cells in vitro following transfer to culture conditions effective to result in such expansion and/or differentiation, e.g., medium containing the appropriate combination of cytokines/growth factors.

While the mechanism is not part of the invention, it will be understood that such rapid stem cell expansion following treatment with an agent effective to block the biological activity of TGF-β indicates that the number of stem cells is increased by the treatment of HSC with a TGF-β blocking agent.

Exemplary culture conditions for maintenance of stem cells by treatment with a TGF-β blocking agent are described herein. However, it will be understood that the optimal survival of stem cells is dependent upon the amount and type of TGF-β blocking agent added to the culture, the time of exposure thereto, and the purity and source of the stem cells (i.e., bone marrow, mobilized peripheral blood or cord blood (murine versus human), or human fetal liver.

In one exemplary approach, the invention provides hematopoietic stem cells that are preserved in culture at 37° C. or 4° C. for at least 18 days, following treatment with a TGF-β blocking agent. Such a hematopoietic stem cell composition finds utility in a variety of applications, including, but not limited to, preserving a population of hematopoietic stem cells ex vivo for subsequent in vivo administration to a subject for purposes of (1) rapid and sustained hematopoietic stem cell replacement therapy, (2) reducing the immune response to allogeneic transplants (i.e., GVHD), (3) treatment of autoimmune disease; (4) gene therapy and (5) treatment of HIV-infection in a subject.

Once a stem cell composition is treated with a TGF-β blocking agent for from a period of time from about 4 to 24 hours, the cells may be maintained in culture at 37° C. for at least 18 days without cell division or differentiation. In general, such a TGF-β blocking agent treated stem cell composition, e.g., a TGF-β antisense oligomer-treated stem cell composition may be maintained in culture until use.

In some cases, stem cells may be frozen in liquid nitrogen following treatment with a TGF-β blocking agent and stored for long periods of time, using standard conditions, such that they can later be thawed and used, e.g., for administration to a patient. In general, the cells are stored in a typical freezing medium, e.g., 10% DMSO, 50% fetal calf serum (FCS), and 40% cell culture medium.

VIII. Exposing Cells ex vivo to A TGF-β Blocking Agent

The invention is based on the discovery that upon in vitro (ex vivo) or in vivo exposure to a TGF-β blocking agent, the time to engraftment is decreased and the extent of HSC self-replication in vivo by the transplanted hematopoietic stem cells is increased.

In one aspect, the invention is directed to methods of modifying the development of hematopoietic stem cells, by obtaining a population of HSCs and exposing them ex vivo to a nuclease-resistant antisense PMO having high affinity to a complementary or near-complementary TGF-β nucleic acid sequence or a sequence which contributes to TGF-β expression in the cells. Typically HSC are exposed to an oligomer antisense to TGF-β for about 4 to 24 hours. However, in some cases the TGF-β blocking agent is maintained in the culture medium for longer periods of time. Following exposure to the antisense oligonucleotide, the HSC may be maintained in culture for 18 days or longer, reinfused into a subject or transferred to culture conditions effective to result in the rapid proliferation of the cells, e.g. medium containing a mixture of exogenously provided cytokines. As can be seen from the data shown in Examples 1 and 2, HSC cultured under the same conditions, but not treated with a TGF-β blocking agent, are not viable after 5 days of culture. In addition, HSC treated with a TGF-β blocking agent then transferred into irradiated C57 mice (950 rads) survived as long as 6 months with donor-derived CD45.1+ cells evident in the peripheral blood of recipient mice. In contrast, when HSC cultured under the same conditions, but not treated with a TGF-β blocking agent, were transferred into irradiated C57 mice (950 rads), the mice did not survive beyond 12 days.

In another aspect, the invention is directed to methods of modifying the development of hematopoietic stem cells, by obtaining a population of HSCs and exposing them ex vivo to a human monoclonal antibody specifically immunoreactive with TGF-β or to Decorin, a naturally occurring inhibitor of TGF-β which is a chondroitin-dermatan sulfate proteoglycan.

Such modified development includes the prolonged survival of HSC in vitro or ex vivo (preserving the viability and differentiation state of the cells). This also preserves the potential for rapid self-replication (expansion) and differentiation when the cells are administered in vivo or transferred to culture conditions effective to result in the rapid proliferation and expansion of the cells.

In one preferred aspect of the invention, the stem cells are human hematopoietic stem cells, characterized by the lack of expression of lineage markers (lin-), and either (a) positive for cell surface expression of CD 34 and KDR and negative for cell surface expression of CD38 or (b) positive for cell surface expression of both CD 34 and Thy1.

A method for rapid in vivo repopulation of the hematopoietic system of a subject and a method for rapid proliferation of stem cells in in vitro culture are further provided by the invention. Such methods include the steps of obtaining a population of cells enriched for stem cells and exposing the stem cells, ex vivo, to a PMO antisense to TGF-β, a PMO antisense to a factor involved in TGF-β expression or a human monoclonal antibody specifically immunoreactive with TGF-β or a protein that contributes to TGF-β expression; under culture conditions, and for a period of time effective to preserve the viability and differentiation state of the cells, followed by either (a) administering the TGF-β blocking agent-treated stem cells to the subject or (b) transferring TGF-β blocking agent-treated stem cells to culture conditions effective to result in the rapid proliferation of the cells, for in vivo and in vitro applications, respectively.

In one aspect, hematopoietic stem cells are obtained from a patient in need of transplantation, e.g., a cancer patient; enriched, treated in vitro (ex vivo) with a TGF-β blocking agent and returned to the patient. In general, such hematopoietic stem cell transplantation is carried out in conjunction with typical therapeutic regiments, i.e., radiation and/or chemotherapy.

Hematopoietic stem cells may be treated ex vivo with a TGF-β blocking agent as described herein, followed by administration to a subject. The subject may be the same individual from whom the hematopoietic stem cells were obtained (autologous transplantation) or a different individual (allogeneic transplantation). In allogeneic transplantation, the donor and recipient are matched based on similarity of HLA antigens in order to minimize the immune response of both donor and recipient cells against the other.

Hematopoietic stem cells for use in the methods of the invention can be extracted from a subject, purified and may be cultured in vitro in the presence of two or more cytokines or in medium lacking exogenously provided cytokines. Preferred cytokines include IL-3, IL-6, SCF and Tpo. It is also preferred that the hematopoietic stem cell population for use in the methods of the invention is both human and allogeneic, or autologous.

The TGF-β blocking agents of the invention are capable of modulating the development of hematopoietic stem cells in vitro. In one aspect, a TGF-β blocking agent of the invention can effectively influence the composition of a culture of hematopoietic stem cells ex vivo such that transfer of the TGF-β blocking agent-treated cells to appropriate culture conditions results in a cell composition comprising more differentiated cells for subsequent re-infusion into a patient. Re-infused ex vivo TGF-β blocking agent-treated stem cells, e.g., hematopoietic stem cells treated with an oligonucleotide antisense to TGF-β, provide a means to rapidly increase the number of both neutrophils and platelets in the circulation of a patient following chemotherapy or radiation therapy.

In one aspect, once extracted and enriched, hematopoietic stem cells may be cultured ex vivo in the presence of a TGF-β blocking agent, e.g., an oligonucleotide antisense to TGF-β. Such an antisense oligomer-treated hematopoietic stem cell culture finds utility in a variety of applications, including, but not limited to, expanding or multiplying the population of lineage-committed progenitor cells and their progeny ex vivo for subsequent in vivo administration to a subject.

Once a culture of TGF-β blocking agent-treated hematopoietic stem cells are obtained, the cells can be used immediately or frozen in liquid nitrogen and stored for long periods of time, using standard conditions, such that they can later be thawed and used, e.g., for administration to a patient. The cells will usually be stored in 10% DMSO, 50% fetal calf serum (FCS), and 40% cell culture medium.

IX. In vivo Administration of Antisense Oligomers

In one aspect, the invention is directed to methods of modifying the development of hematopoietic stem cells in vivo in a patient, by administering to the patient a therapeutically effective amount of a TGF-β blocking agent-containing pharmaceutical composition, as described herein, e.g., a pharmaceutical composition comprising an oligomer antisense to TGF-β.

The antisense oligomers of the invention can be effective in the treatment of patients by modulating the cell division and/or differentiation properties of HSC in the patient.

In one embodiment, a subject is in need of an increased number of differentiated hematopoietic cells, such as neutrophils and/or platelets, e.g., following chemotherapy or radiation therapy. In this embodiment, a TGF-β blocking agent is administered to the subject in a manner effective to result in an increase in the number of both neutrophils and platelets in the circulation of the subject.

It will be understood that in vivo administration of such a TGF-β blocking agent to a subject using the methods of the invention can provide a means to increase the population of lineage committed progenitor cells and their progeny, dependent upon, (1) the duration, dose and frequency of antisense administration, and (2) the general condition of the subject.

A. Treating Patients

Effective delivery of an antisense oligomer to the target nucleic acid is an important aspect of the methods described herein. In accordance with the invention, such routes of antisense oligomer delivery include, but are not limited to, inhalation; transdermal delivery; various systemic routes, including oral and parenteral routes, e.g., intravenous, subcutaneous, intraperitoneal, or intramuscular delivery.

Similarly, effective delivery of a human anti-TGF-β monoclonal antibody to a patient is an important aspect of the methods described herein. In accordance with the invention, such routes of delivery include, but are not limited to, various systemic routes, including parenteral routes, e.g., intravenous, subcutaneous, intraperitoneal, or intramuscular.

It is appreciated that any methods which are effective to deliver a TGF-β blocking agent to hematopoietic stem cells or to introduce the agent into the bloodstream are also contemplated.

In preferred applications of the method, the subject is a human subject and the methods of the invention are applicable to treatment of any condition wherein promoting the rapid differentiation and replication of hematopoietic stem cells would be effective to result in an improved therapeutic outcome for the subject under treatment.

The invention provides a method to rapidly repopulate the hematopoietic system of a subject, by exposing hematopoietic stem cells to a TGF-β blocking agent (as further described herein), under conditions suitable to promote differentiation and replication of hematopoietic stem cells.

It will be understood that an effective in vivo treatment regimen using a TGF-β blocking agent in the methods of the invention will vary according to the frequency and route of administration as well as the condition of the subject under treatment. Accordingly, such in vivo therapy will generally require monitoring by tests appropriate to the condition being treated and a corresponding adjustment in the dose or treatment regimen in order to achieve an optimal therapeutic outcome.

B. Administration of Anti-TGF-β Antisense Oligomers

Transdermal delivery of an antisense oligomer may be accomplished by use of a pharmaceutically acceptable carrier. One example of morpholino oligomer delivery is described in PCT patent application WO 97/40854, incorporated herein by reference.

In one preferred embodiment, the oligomer is an anti-TGF-β morpholino oligomer, contained in a pharmaceutically acceptable carrier, and delivered orally. In a further aspect of this embodiment, the antisense oligomer is administered at regular intervals for a short time period, e.g., daily for two weeks or less. However, in some cases the antisense oligomer is administered intermittently over a longer period of time.

Typically, one or more doses of TGF-β antisense oligomer are administered, generally at regular intervals for a period of about one to two weeks. Preferred doses for oral administration are from about 1 mg oligomer/patient to about 25 mg oligomer/patient (based on an adult weight of 70 kg). In some cases, doses of greater than 25 mg oligomer/patient may be necessary. For IV administration, the preferred doses are from about 0.5 mg oligomer/patient to about 10 mg oligomer/patient (based on an adult weight of 70 kg).

The antisense agent is generally administered in an amount sufficient to result in a peak blood concentration of at least 200–400 nM antisense oligomer.

In general, the method comprises administering to a subject, in a suitable pharmaceutical carrier, an amount of a TGF-β morpholino antisense oligomer effective to inhibit expression of TGF-β or a factor that contributes to TGF-β expression.

It follows that a morpholino antisense oligonucleotide composition may be administered in any convenient vehicle, which is physiologically acceptable. Such an oligonucleotide composition may include any of a variety of standard pharmaceutically accepted carriers employed by those of ordinary skill in the art. Examples of such pharmaceutical carriers include, but are not limited to, saline, phosphate buffered saline (PBS), water, aqueous ethanol, emulsions such as oil/water emulsions, triglyceride emulsions, wetting agents, tablets and capsules. It will be understood that the choice of suitable physiologically acceptable carrier will vary dependent upon the chosen mode of administration.

In some instances liposomes may be employed to facilitate uptake of an antisense oligonucleotide into cells. (See, e.g., Williams, 1996; Lappalainen, et al., 1994; Uhlmann, et al., 1990; Gregoriadis, 1979.) Hydrogels may also be used as vehicles for antisense oligomer administration, for example, as described in WO 93/01286. Alternatively, an oligonucleotide may be administered in microspheres or microparticles. (See, e.g., Wu et al., 1987).

Sustained release compositions are also contemplated within the scope of this application. These may include semipermeable polymeric matrices in the form of shaped articles such as films or microcapsules.

C. Monitoring Treatment

The efficacy of a given therapeutic regimen involving the methods described herein, may be monitored, e.g., by conventional FACS assays for the phenotype of cells in the circulation of the subject under treatment. Such analysis is useful to monitor changes in the numbers of cells of various lineages, in particular, neutrophil and platelet recovery post transplant in response to administration of a TGF-β blocking agent-treated stem cell composition and/or a TGF-β blocking agent.

Phenotypic analysis is generally carried out using monoclonal antibodies specific to the cell type being analyzed. The use of monoclonal antibodies in such phenotypic analyses is routinely employed by those of skill in the art for cellular analyses and monoclonal antibodies specific to particular cell types are commercially available.

Hematopoietic stem cells may be characterized phenotypically as detailed above. Such phenotypic analyses are generally carried out in conjunction with biological assays for various cell types of interest, for example (1) hematopoietic stem cells (LTCIC, cobblestone forming assays, assays for HPP-CFCs, or NOD-SCID-hu in vivo assays), (2) granulocytes or neutrophils (clonal agar or methyl cellulose assays wherein the medium contains G-CSF or GM-CSF), (3) megakaryocytes (clonal agar or methyl cellulose assays wherein the medium contains TPO, IL-3, IL-6 and IL-11), and (4) erythroid cells (clonal agar or methyl cellulose assays wherein the medium contains EPO and SCF or EPO, SCF and IL-3).

It will be understood that the exact nature of such phenotypic and biological assays will vary dependent upon the condition being treated and whether the treatment is directed to enhancing the population of hematopoietic stem cells or the population of cells of a particular lineage or lineages.

The TGF-β blocking agent treatment regimen may be adjusted (dose, frequency, route, etc.), as indicated, based on the results of the phenotypic and biological assays described above.

X. Utility/Applications of the Method

The hematopoietic stem cell methods described herein find utility in a variety of applications. For example, an in vitro or ex vivo stem cell composition which has been treated with a TGF-β blocking agent may serve as a source of cells for rapid repopulation of a subject following in vivo administration and for rapid in vitro expansion/differentiation following transfer to the appropriate culture conditions. In addition, such TGF-β blocking agent-treated stem cells provide a source of stem cells for various cellular transplantation and gene therapy applications.

TGF-β blocking agent-treated stem cells also find utility in repopulating non-hematopoietic tissues in vivo, including, but not limited to liver. Further uses include the use of TGF-β blocking agent-treated stem cells to initiate in vitro cultures of expanded and/or differentiated stem cells for any of a number of uses for which clinicians currently rely on cell preparation containing small numbers of stem cells which are used soon after they are prepared.

Such in vitro or ex vivo TGF-β blocking agent-treated stem cell compositions also find utility in both autologous and allogeneic hematopoietic engraftment when administered to a patient, where the cells are freed of neoplastic disease and graft-versus-host disease can be avoided.

Alternatively, such an in vitro or ex vivo TGF-β blocking agent-treated stem cell compositions may be used for gene therapy to treat any of a number of diseases. In such cases, genetically modified stem cells containing a transgene of interest, e.g., directed toward a particular disease target, are prepared in vitro and reinfused into a subject such that the cell type(s) targeted by the disease are rapidly repopulated by differentiation of cells in the stem cell composition following reinfusion into the subject.

A. Autologous Transplantation

Autologous hematopoietic stem cell transplantation has been used to treat many solid tumors, including but not limited to, breast cancer and ovarian cancer. Prior to autologous stem cell transplantation the patient may or may not be treated with chemotherapy and/or radiation. In general, during this time the patient is immunocompromised and protective isolation is required.

B. Allogeneic Transplantation

Allogeneic transplantation has been used to treat patients with leukemia, aplastic anemia, lymphomas (Hodgkin's disease and non-Hodgkin's lymphoma), and immune deficiency diseases. An allogeneic stem cell transplantation protocol is similar to that used for autologous transplantation with the exception that in allogeneic transplantation, the donor and recipient must be matched based on the similarity of HLA cell surface antigens in order to minimize the immune response of both donor and recipient cells against the other.

The methods of the present invention provide a means to accelerate the recovery of a patient following autologous or allogeneic stem cell transplantation, by exposure of hematopoietic stem cells to a TGF-β blocking agent, which results in rapid and sustained repopulation of the hematopoietic system, e.g., by resulting in a rapid increase in the number of neutrophils and/or platelets, in the subject following infusion of TGF-β blocking agent-treated stem cells into the patient.

C. Graft Versus Host Disease (GVHD)

GVHD is a frequent complication of allogeneic transplantation. About half of the patients undergoing an allogeneic bone marrow transplant develop some form of GVHD. In GVHD, the donor's mount an immune response against the recipient's organs and tissue. Patients with GVHD have an increased susceptibility to infection.

GVHD is caused by T-cells, which recognize the patient's cells as being foreign. T-cells are able recognize differences based on human leukocyte antigens (HLA). Even when the donor and recipient have similar HLA types, many minor markers differ between them. Hence, graft versus host disease (GVHD) is a potential problem and treatment to minimize the GVH response is part of the therapeutic regimen for most transplants.

Accordingly, stem cell transplantation, is often accompanied by T-cell depletion alone, or in combination with hematopoietic stem cell enrichment and drug therapy for prevention of GVHD, e.g., administration of cyclosporin (an immunosuppressive drug), alone or together with mehtotrexate.

The methods of the present invention provide a means to limit the occurrence of GVHD by exposure of hematopoietic stem cells to a TGF-β blocking agent, and transfer of the treated stem cells to conditions which results in rapid differentiation of the cells. Upon re-infusion of the TGF-β blocking agent-treated stem cells into the patient, rapid and sustained repopulation of the hematopoietic system results.

Stem cells within such an ex vivo expanded stem cell composition lack immunological memory of self and non-self antigens, such that transplantation of the hematopoietic stem cells into an allogeneic host is unlikely to result in GVHD.

D. Autoimmune Disease

As hematopoietic stem cells differentiate they are exposed to the various antigens present on the cells and tissue of the host and immunological tolerance is established during T cell development within the thymus. In general, T cells that would be reactive to host proteins do not survive. However, in some cases, the immune system may recognize self antigens as foreign resulting in an immune reaction against one or more endogenous antigens which leads to an autoimmune condition or disease.

Exemplary autoimmune conditions include organ specific forms wherein the immune response is directed against, e.g., the cells of the adrenal glands, causing Addison's disease, against the thyroid causing auto-immune thyroiditis (Hashimoto's disease) or against the beta cells of the islets of Langerhans in the pancreas, resulting in insulin-dependent diabetes mellitus; and non-specific forms wherein the immune response is directed against an antigen that is ubiquitous, e.g., an immune reaction against DNA, resulting in the disease systemic lupus erythematosus. Further examples include, Sjogren's syndrome, caused by the production of auto-antibodies against salivary ducts, rheumatoid arthritis. Autoimmunity may be the result of attack by antibodies, T-cells or both.

The invention provides methods for the treatment of autoimmune disease. In such methods, an enriched population of HSC are obtained from a patient, followed by treatment of the patient with chemotherapy, radiation therapy or other means to deplete the patient of residual T-cells. An enriched population of HSC derived from the patient or an allogeneic donor are cultured ex vivo in the presence of a TGF-p blocking agent resulting in maintenance of viable stem cells in vitro at 37° C. or 4° C., followed by reinfusion of the TGF-p blocking agent-treated stem cells into the patient resulting in repopulation of the hematopoietic system of the patient by about 1 to 3 weeks post transplantation.

Such an in vitro TGF-β blocking agent-treated hematopoietic stem cell composition lacks immunological memory of self antigens, such that transplantation of the stem cell composition finds utility in the treatment of patients with an autoimmune disease, in order to minimize or eliminate the autoimmune condition.

It will be understood that such ex vivo hematopoietic stem cell treatment and re-infusion is generally used in combination with additional therapeutic intervention to minimize the autoimmune response. Such additional treatment components include compositions and procedures known in the art for the treatment of autoimmune disease.

E. Gene Therapy Applications

Gene therapy which encompasses gene correction therapy and transfer of therapeutic genes is being applied to the treatment of cancer, infectious diseases, multigenic diseases, and acquired diseases.

Exemplary targets include, but are not limited to cancer such as prostate cancer, breast cancer, lung cancer, colorectal cancer, melanoma and leukemia; infectious diseases, such as HIV, monogenic diseases such as CF, hemophilia, phenylketonuria, ADA, familial hypercholesterolemia, and multigenic diseases, such as restenosis, ischemia, and diabetes.

Stem cells are an optimal vehicle for gene therapy, given that it has been shown that hematopoietic stem cells are capable of maintaining their numbers in vivo without exhaustion, can repopulate at least the entire hematopoietic system and that mature hematopoietic cells circulate throughout the body providing for effective delivery of a corrected gene (e.g., adenosine deaminase deficiency).

Although gene transfer into cells is possible in vivo, it is simpler and more easily controlled ex vivo or in vitro, rendering ex vivo cultured hematopoietic stem cells extremely useful for therapeutic gene therapy. (See, e.g., Beutler E, 1999; Dao M, 1999.)

In one exemplary approach, a therapeutic gene therapy regimen includes the steps of obtaining a population of cells from a subject, enriching the cells for HSC, ex vivo treatment of the stem cell enriched population with a TGF-β blocking agent, transfer of the TGF-β blocking agent-treated stem cell population to culture conditions that facilitate expansion and differentiation of the stem cells (i.e. a culture consisting of fibroblasts, endothelial cells and megakaryocytes plus thrombopoietin and IL-6, (See, e.g., Yagi et. al., 1999), transduction of the cells with a vector containing a gene of interest, and introduction of the treated, transduced cells into a subject.

The transfer of genetic material into cells can be achieved by physical and chemical methods or by the use of recombinant viruses. In the case of ex vivo transfer, chemical and physical methods such as calcium phosphate, electroporation and pressure mediated transfer of genetic material into cells are often used. Several recombinant viral vectors which have been used for effective delivery of genes into mammalian cells include viral vectors, for example, retroviral vectors, adenovirus vectors, adenovirus-associated vectors (AAV), herpes virus vectors, pox virus vectors; non-viral vectors, for example naked DNA delivered via liposomes, receptor-mediated delivery, calcium phosphate transfection, electroporation, particle bombardment (gene gun), or pressure-mediated gene delivery. Various reports have been presented regarding the efficacy of gene therapy for the treatment of monogenic diseases, early stage tumors, and cardiovascular disease. (See, e.g., Blaese et al., 1995; Wingo et al., 1998; Dzau V, 1998; and Isner, 1998.)

Various exemplary utilities have been described for TGF-β blocking agent treated-hematopoietic stem cells, however the present invention is applicable to any of a number of situations where rapid repopulation of the hematopoietic system of a subject is desired.

All patent and literature references cited in the present specification are hereby incorporated by reference in their entirety.

The following examples illustrate but are not intended in any way to limit the invention.

Materials And Methods

Murine HSC Preparation and Culture with Antibodies

In general, murine LTR-HSC are purified from B6SJL mice (CD45.1+) by flushing cells from femurs of male B6.SJL-Ptprc$^a$ Pep3$^b$/BoyJ (Ly5.1) (CD45.1) (B6.SJL) mice (Jackson Labs, Bar Harbor, Me.) with medium consisting of IMDM medium (Gibco BRL Life Technologies, Gaithersburg, Md.) supplemented with 20% heat-inactivated defined horse serum (HyClone Laboratories, Logan, Utah), 100 units/ml penicillin-10 µg/ml streptomycin, 2 mM L-glutamine. Low density cells are enriched using 1.080 g/ml Nycodenz separation medium (Nycomed Pharma AS OSLO, Norway), followed by isolation of the lin- cell population using Dynal Bead depletion employing lineage-specific monoclonal antibodies. Lin⁻ cells are then incubated with Hoescht 33342 (Ho, final concentration 10 mM) for 1 hr at 37 degrees and Rhodamine 123 (Rh, final concentration 0.1 µg/ml) is added during the final 20 minutes (Wolf, et al., 1993). Cells are then labeled with phycoerythrin (PE)-conjugated anti-c-kit antibody (1 µg/ml final). Finally, propidium iodide (PI) is added (2 µg/ml final concentration) for detection of dead cells and cells are analyzed and sorted by FACS within 1–4 hours. Cell sorting has been performed on a FACStar Plus flow cytometer (or Coulter Elite or Ortho 50) equipped with dual argon lasers, and an automated cell delivery unit (ACDU). Monochromatic light at 351–364 nm and 488 nm is used for Ho and Rh 123 excitations, respectively. Forward light scatter is detected using 488 bp10 and ND 1.0 filters. Ho emission is detected using a 515 Ip filter in order to maximize signals from hematopoietic cells (Goodell et al; Bartelmez et al., unpublished observations). Rh 123 emission was detected using a 530 bp20 filter, PE emission using a 575 bp20 filter, PI emission using a 610 Ip filter. Cells are gated using the following steps: first, forward light scatter and PI fluorescence are analyzed and viable cells (PI negative) selected. Next, gates are set at the various percentages of Rh fluorescence using a 4-log amplifier: the lowest 10% (defined as $Rh^{low}$) and the middle 40% of the peak (defined as $Rh^{high}$). Then $Rh^{low}$ and $Rh^{high}$ cells are then analyzed for their linear Ho fluorescence and logarithmic PE-anti-c-kit receptor fluorescence. $Rh^{low}$ and $Rh^{high}$ cells are sorted as individual cells into 96-well plates or collected in bulk.

LTR-HSC enriched in this manner have been intensively characterized and have the following phenotype: "lin-, Rh-123 low, Ho-33342 low, c-kit+, Sca-1+, Thy-1 low, CD-34 negative, M 4.1 negative" (Bartelmez S, et al., 2000).

LTR-HSC, characterized as described above are sorted directly into phosphate buffered saline (PBS) for all experiments in which LTR-HSC are transplanted at time 0 (T=0), or if the cells are cultured, the LTR-HSC are sorted directly into basic culture medium for LTR-HSC which generally contains (1) Fisher's medium, 20% horse serum, $10^{-6}$ M hydrocortisone (HC) or (2) IMDM medium plus 12.5% horse serum and 12.5% fetal bovine serum, $10^{-6}$ M hydrocortisone or (3) serum-free medium (QBSF-58, Quality Biological Inc., Gaithersburg. MD). In cultures containing exogenously provided cytokines, the culture medium also contains one or more of interleukin-3,6,11,12 (IL-3,6,11,12), stem cell factor (SCF), or thrombopoietin (Tpo). In experiments in which cells were directly transplanted prior to short in vitro exposure to a TGF-β blocking agent, such treatment took place in PBS, not in culture medium.

One exemplary TGF-β blocking agent is an oligomer antisense to TGF-β (SEQ ID NO:1), added to the culture medium at a concentration of from about 5 to 25 µM.

Human HSC Preparation and Culture with Antibodies

In general, human HSC are purified from umbilical cord blood samples collected immediately after delivery, from mobilized peripheral blood or bone marrow as further described above. In general, CD34+ cells are purified using immunomagnetic beads (Dynel), suspended in PBS/BSA (0.2%) and incubated with an anti-CD34 fluorescein isothiocyanate (FITC)-conjugated monoclonal antibody (mAb; e.g., 8G 12 clone; Becton Dickinson, San Jose, Calif.) and an anti-CD38 phycoerythrin (PE)-conjugated mAb (e.g., HB-7 clone; Becton Dickinson) for 30 minutes at 4° C., then washed twice. Isotype non-specific FITC- and PE-IgG1 are used as negative controls. The CD34+ $CD38^{low}$ cell population is isolated by FACS (with the $CD38^{low}$ subpopulation is defined as the 10% of CD34+ cells with the lowest intensity of CD38 antigen expression) and deposited into 96-well plates containing medium using a Vantage fluorescence activated cell sorter (FACS; Becton Dickinson) equipped with an automatic cell deposition unit.

HSC are characterized by FACS analysis and cultured in semi-solid or liquid medium using techniques generally known in the art.

In cultures containing exogenously provided cytokines, the culture medium typically includes at least two cytokines selected from the following list: IL-3, IL-6, IL-11, IL-12, SCF, flt-3, Tpo and/or TGF-beta. In general, hematopoietic growth factors are purchased from Peprotech, with the exception of TGF-β (which was a gift from Bristol-Meyers Squibb). In general, cytokines are used at concentration of approximately 10 ng/ml for IL-6, IL-3, GM-CSF and TGF-β and 50 ng/ml for SCF and flt-3, respectively.

Exemplary TGF-β blocking agents include PMOs antisense to TGF-β ligand (SEQ ID NO:1), TGF-β Type II receptor (SEQ ID NO:2), and the TGF-β splice acceptor junction between intron 5 and exon 6 (SEQ ID NO:5). In general, such oligomers are added to the culture medium at a concentration of about 25 µM.

Immunophenotyping of LTBMC cells. LTBMC cells are centrifuged and resuspended in 1% (w/v) bovine serum albumin in Dulbecco's phosphate-buffered saline. Fluorochrome-conjugated monoclonal antibodies to various mouse CD antigens, or biotinylated anti-mouse CD34 and FITC- or PE-conjugated strepavidin (Pharmingen, San Diego, Calif.) are incubated with the cells on ice (1 µg antibody/1-2×$10^5$ cells). Cells are washed and analyzed by flow cytometry (FACScan, Becton-Dickinson, Mountain View, Calif.) in the presence of propidium iodide to exclude dead cells.

Clonogenic cell assays. Colony formation assays are performed in soft agar cultures (murine) or methylcellulose (human) in the presence of recombinant cytokines (R & D Systems or PeproTec, Rose Hill, N.J.) (Sitnicka et al., 1996). Two to five thousand cells are added per ml of culture and plated in 35 mm dishes. Cultures are incubated for 12 days, and colonies counted using an inverted microscope. In some experiments, cells are plucked from colonies and their morphology assessed after staining with Giemsa. Cytokines are used at the following concentrations: for CFC, 5 ng/ml mouse GM-CSF and 10% (v/v) L929 supernatant (mouse M-CSF); for HPP-CFC, 50 ng/ml rat SCF, 20 ng/ml human IL-6, and 10 ng/ml mouse IL-3.

Colony formation assays for murine versus human CFC differ in that human HPP-CFC are carried out in methylcellulose medium (Stem Cell Tech., Cat. No. H4435), in the presence of SCF (50 ng/ml), IL-3 (50 ng/ml), IL-6 (20 ng/ml), erythropoietin (EPO, 1 unit/ml) and GM-CSF (5 ng/ml). (See, e.g., Andrews et al., 1990.)

LTBMC assay conditions for human cells generally include commercially available media, e.g., Fishers medium; horse serum (Hyclone, Logan, Utah) from a lot selected based on optimal HSC generation in murine Tpo-LTMC assays; purified recombinant human Tpo (rhuTpo, Genentech, South San Francisco, Calif.); hydrocortisone; a human stromal cell component which includes, but is not limited to, cells of mesenchymal origin, including fibroblasts, adipocytes, endothelial cells; and megakaryocytes.

Transplants and competitive repopulation assays. Cells from B6.5JL mice (CD45.1) were harvested, washed, and used unfractionated for transplant. For each test sample, 2–10 recipient C57Bl6 mice (CD45.2) were irradiated (950 rad, $^{137}$Cesium source) and transplanted by injection via the tail vein with the indicated number of test cells mixed with $4\times10^5$ fresh unfractionated CD45.2 marrow cells. Animals were maintained in microisolator cages in an SPF facility. Peripheral blood samples were obtained by retroorbital bleeding at various times post-transplant. Expression of the donor CD45.1 allele and lineage specific antigens was assessed by two-color flow cytometry analysis of peripheral blood leukocytes using directly labeled monoclonal antibodies as described above for cultured cells. The frequency of long-term repopulating units was estimated using the maximum likelihood model that requires limiting dilution cell transplants of the test cells (Taswell, 1981).

In vivo assays for human HSC. In vivo assays for human HSC may be carried out by introducing approximately 10,000–20,000 purified lineage negative CD34+ cells derived from culture into an in utero fetal sheep assay, as described in Zanjani et al., 1995.

The following examples illustrate but are not intended in any way to limit the invention.

EXAMPLE 1

Survival of Single LTR-HSC Treated with TGF-β Antisense Oliqonucleotides in the Absence of Exogenously Provided Growth Factors Long-term repopulating hematopoietic stem cells (LTR-HSC) (lin-, Rh low, Ho low, c-kit+, Sca-1+, Thy-1 low, CD 34 negative cells purified from murine bone marrow) were sorted as single cells into 96 well round-bottom plates. Wells actually containing single cells were verified and mapped by direct microscopy, given that cell sorters are not 100% efficient. Wells were observed daily for light refractile cells. At day five, viable cells were determined by culture in medium containing SCF to a final concentration of 50 ng/ml, 20 ng/ml IL-6 and 50 ng/ml IL-3. Cells that divided one or more times over the next 7 days in the presence of these cytokines/growth factors were considered to be viable at the time of cytokine/growth factor addition. Cells were cultured in IMDM medium containing 20% selected horse serum and $10^{-6}$ hydrocortisone. In some cases, at day 0, a morpholino antisense oligomer (PMO) was also added to a final concentration of 25 μM, exemplified by a PMO specific to the Type II TGF-β receptor presented as SEQ ID NO:2 (AVI BioPharma lot # 98MY20-Z, A5). A tel-PDGFRB scramble control PMO (corresponding to the sequence for the junction of the tel and PDGF-receptor translocated fusion gene) served as a negative control (SEQ ID NO:3; AVI BioPharma lot # 98SE02-R, E1).

The results indicate that treatment of LTR-HSC with a PMO directed to the Type II TGF-β receptor resulted in survival of LTR-HSC in the absence of exogenously provided growth factors, while untreated and PMO scramble control-treated HSC did not survive.

TABLE 1

Effect of PMOs on the survival of single LTR-HSC in the absence of exogenously provided growth factors

| Treatment[2] | Proportion Of Single LTR-HSC[1] Viable At Day 5 |
|---|---|
| None-medium alone | 0% (0/81) |
| PMO Scrambled control[3] | 2% (2/78) |

TABLE 1-continued

Effect of PMOs on the survival of single LTR-HSC in the absence of exogenously provided growth factors

| Treatment[2] | Proportion Of Single LTR-HSC[1] Viable At Day 5 |
|---|---|
| PMO Type II TGF-beta receptor[5] | 29% (23/79) |

EXAMPLE 2

Rapid Repopulation and Rescue of Lethally Irradiated Mice by Transplantation with TGF-β PMO-treated LTR-HSC 100 LTR-HSC were cultured without growth factors but in the presence of an oligomer antisense to TGF-β or a murine monoclonal anti-TGF-β antibody, then assayed in a competitive repopulation assay, as detailed above. The results indicate that a substantial proportion of the surviving cells retained their LTR ability (Table 2, below).

In one experiment, LTR-HSC (lin-, Rh low, Ho low, c-kit+) were purified from B6SJL mice (CD45.1+); and incubated ex vivo (1) in culture medium alone (None); or (2) treated with a morpholino antisense (MAS) oligomer to TGF-β for 24 hours at room temperature, washed, then transplanted into irradiated C57 mice (950 rads; MAS TGF-β).

The results of a representative experiment are shown below in Table 2, and indicate that LTR-HSC treated with a morpholino oligomer antisense to TGF-β, rapidly and substantially engrafted lethally irradiated recipients.

LTR-HSC (lin-, Rh low, Ho low, c-kit+, Sca-1+, Thy-1 low, CD34-) were either directly transplanted into C57 mice (950 rads irradiation) or placed into culture at 60 cells per 96 round bottom well in medium containing 25 μM of a TGF-β morpholino antisense (MAS) oligomer, in IMDM medium containing Tpo (20 ng/ml), 20% horse serum at 37° C. (and lacking additional exogenously provided growth factors or cytokines). After 24 hours, cells were counted and the total cells of one well was directly transplanted into an irradiated C57 mouse (950 rads; in the absence of support or competitor cells).

The results shown in Table 2, below, show that 75% (9/12) or 66% (6/9) of the mice survived which received HSC treated with a TGF-β MAS survived up to greater than 6 months post-transplant. In contrast, when untreated LTR-HSC were transplanted into irradiated C57 mice (950 rads), the mice did not survive beyond 12 days.

Following intravenous administration of LTR-HSC treated with a morpholino oligomer antisense to TGF-β into irradiated C57 mice (950 rads), the percentage of donor-derived CD45.1+ cells ("% CD 45.1 Donor Chimera") was evaluated in the peripheral blood of recipient mice at 3 weeks, 6 weeks, 3 months and 6 months post transplant. (See Table 2). When LTR-HSC were treated with a morpholino oligomer antisense to TGF-β prior to transplantation, from 51% to 90% of the cells were determined to be of the CD 45.1 donor cell phenotype.

TABLE 2

Rapid Repopulation and Rescue of Lethally Irradiated Mice by limiting numbers of LTR-HSC treated with a TGF-β MAS oligomer

| Treatment | Number of Cells Transplanted T = 0 | Number of Cells Transplanted T = 1 day | Proportion Mice Surviving | % CD 45.1 Donor Chimera 3 weeks | % CD 45.1 Donor Chimera 6 weeks | % CD 45.1 Donor Chimera 3 months | % CD 45.1 Donor Chimera 6 months |
|---|---|---|---|---|---|---|---|
| None | $60^{\pm 0.5}$ | NA | None | NA | NA | NA | NA |
| MAS TGF-β | NA | $105^{\pm 0.5}$ | 75%(9/12) | $51^{\pm 18}$ | $77^{\pm 13}$ | $87^{\pm 14}$ | $90^{\pm 12}$ |

These results demonstrate that rapid engraftment of LTR-HSC following treatment with a morpholino oligomer antisense to TGF-β did not impair the long term repopulating ability of the donor cells as measured by a sustained high percentage of donor chimeras as long as 6 months following transplantation.

The experimental results presented above demonstrate (1) that treatment of HSC with a MAS directed to the type II TGF-β receptor was effective to promote the survival of LTR-HSC in culture in the absence of exogenously provided cytokines; and (2) that treatment of HSC with a MAS directed to TGF-β is effective to promote both rapid and sustained repopulation of the hematopoietic system of lethally irradiated recipients.

TABLE 3

Sequences Provided in Support of the Invention

| Description | SEQ ID NO |
|---|---|
| Oligo antisense to TGF-β1:<br>5' GAG GGC GGC ATG GGG GAG GC 3'. | 1 |
| Oligo antisense to TGF-β Type II receptor: AVI sequence ID #0-1-0-386<br>5'- GAG CCA TGG CAG CCC CCG TCG 3' | 2 |
| tel-PDGFRB scramble: AVI sequence ID#0-1-0-459<br>5' GCT GTG CGC GCG CCT TCT CTA TG 3' | 3 |
| Oligo antisense to RB protein: 5' GTG AAC GAC ATC YCA TCT AGG-3' | 4 |
| Oligo antisense to TGF-β1 splice junction:<br>5' GCA GCA GTT CTT CTC CGT GG 3' | 5 |

It is claimed:

1. A method of decreasing the time for hematopoietic reconstitution of a patient following chemotherapy or radiation therapy, comprising:
   (a) obtaining a population of cells containing human stem cells from a subject;
   (b) enriching for the human stem cells in said population;
   (c) exposing the enriched stem cell population, ex vivo, to an oligomer antisense to TGF-β, under culture conditions and for a period of time effective to block the effect of TGF-β on replication and/or differentiation of said stem cells;
   (d) culturing the antisense oligomer treated stem cells to obtain cultured TGF-β blocking agent-treated stem cells, wherein the viability and differentiation state of said stem cells is maintained for at least 5 days; and
   (e) administering said cultured TGF-β blocking agent-treated stem cells to a subject, wherein the time required for in vivo reconstitution of at least one hematopoietic lineage is reduced relative to that of a subject who received stem cells not treated with an oligomer antisense to TGF-β.

2. The method of claim 1, wherein the human stem cells in said enriched stem cell population are characterized as lacking the expression of lineage markers (lin-), and are either (a) positive for cell surface expression of CD 34 and KDR and negative for cell surface expression of CD38 or (b) positive for cell surface expression of both CD 34 and Thy1.

3. The method of claim 1, wherein the antisense oligomer is a morpholino oligomer characterized by,
   (a) a backbone which is substantially uncharged;
   (b) the ability to hybridize with the complementary sequence of a target RNA with high affinity at a Tm greater than 50° C.;
   (c) nuclease resistance; and
   (d) the capability for active or facilitated transport into cells.

4. The method of claim 3, wherein the linkage is a phosphorodiamidate linkage represented at FIG. 2B, where X=NH$_2$, Y=O, and Z=O.

5. The method of claim 3 wherein the antisense oligomer has a length of from 12 to 25 bases.

6. The method of claim 4 wherein the antisense oligomer has a sequence presented as SEQ ID NO:1, SEQ ID NO:2 or SEQ ID NO:5.

* * * * *